(12) United States Patent
Hirata

(10) Patent No.: US 7,549,958 B2
(45) Date of Patent: Jun. 23, 2009

(54) ENDOSCOPE APPARATUS

(75) Inventor: Yasuo Hirata, Tokyo (JP)

(73) Assignee: Olympus Corporation (JP)

( * ) Notice: Subject to any disclaimer, the term of this patent is extended or adjusted under 35 U.S.C. 154(b) by 721 days.

(21) Appl. No.: 11/052,616

(22) Filed: Feb. 7, 2005

(65) Prior Publication Data

US 2005/0177027 A1 Aug. 11, 2005

(30) Foreign Application Priority Data

Feb. 9, 2004 (JP) ............................. P2004-032490
Feb. 9, 2004 (JP) ............................. P2004-032491

(51) Int. Cl.
*A61B 1/06* (2006.01)

(52) U.S. Cl. ..................... 600/179; 600/178; 600/172; 439/86

(58) Field of Classification Search ............... 600/129, 600/175, 178–180; 200/514, 516; 439/86, 439/586, 591; 362/205, 574
See application file for complete search history.

(56) References Cited

U.S. PATENT DOCUMENTS

| 3,871,737 | A | * | 3/1975 | Dorrell et al. ................. 439/88 |
|---|---|---|---|---|
| 4,404,964 | A | * | 9/1983 | Kambara ..................... 600/163 |
| 5,191,388 | A | * | 3/1993 | Kilham ....................... 356/335 |
| 5,413,508 | A | * | 5/1995 | Obara ......................... 439/729 |
| 5,924,978 | A | * | 7/1999 | Koeda et al. ................. 600/178 |
| 6,007,485 | A | * | 12/1999 | Koeda et al. ................. 600/178 |
| 6,036,636 | A | | 3/2000 | Motoki et al. ................ 600/146 |
| 6,135,947 | A | * | 10/2000 | Watanabe et al. ............ 600/178 |
| 6,307,946 | B1 | * | 10/2001 | Fujimoto et al. ............. 381/355 |
| 6,685,632 | B1 | * | 2/2004 | Hu et al. ...................... 600/234 |
| 6,796,939 | B1 | | 9/2004 | Hirata et al. ................. 600/179 |
| 7,140,893 | B2 | * | 11/2006 | Abe et al. .................... 439/144 |
| 2001/0016435 | A1 | * | 8/2001 | Fujimura ..................... 439/66 |
| 2002/0137987 | A1 | * | 9/2002 | Watanabe et al. ............ 600/178 |
| 2002/0149928 | A1 | * | 10/2002 | Watterson et al. ........... 362/184 |

FOREIGN PATENT DOCUMENTS

| JP | 10-216085 | | 8/1998 |
|---|---|---|---|
| JP | 10216085 A | * | 8/1998 |
| JP | 10-328131 | | 12/1998 |

* cited by examiner

*Primary Examiner*—John P Leubecker
*Assistant Examiner*—Samuel Candler
(74) *Attorney, Agent, or Firm*—Ostrolenk Faber LLP

(57) ABSTRACT

An endoscope apparatus includes a light emitting diode provided at a tip end of an insertion part, and an electrical power supplying circuit of the light emitting diode which is detachably connected to a main power supply, the electrical power supplying circuit having an energizing controlling device of the light emitting diode, which operates upon being connected and disconnected to the main power supply.

10 Claims, 26 Drawing Sheets

ENDOSCOPE APPARATUS

BACKGROUND OF THE INVENTION

1. Field of the Invention

The present invention relates to an endoscope apparatus having a light emitting diode (LED) for illumination, etc., at the tip end of an insertion part inserted into a lumen, for an industrial use or a medical use, etc.

Priority is claimed on Japanese Patent Application No. 2004-032490, filed Feb. 9, 2004, and Japanese Patent Application No. 2004-032491, filed Feb. 9, 2004, the contents of which are incorporated herein by reference.

2. Description of Related Art

In general, an endoscope apparatus currently used industrially or medically is equipped with a long insertion part which is inserted into a lumen. Moreover, in such an endoscope apparatus, in order to illuminate the target for observation in a lumen and to make observation and image pick-up easy, there is an illumination device at the tip end of the insertion part.

In recent years, an illumination device having a light emitting diode (which is referred as "LED", hereinafter) is proposed. Moreover, for example, as disclosed in Japanese Patent Application First publication No. Hei 10-216085, an endoscope having a plurality of adapters, each of which is detachably attached to the tip end of the insertion part, and is equipped with an LED illumination device and a separate optical system, is proposed. This endoscope is constituted so that an optimal adapter can be selected from a plurality of kinds of adapters prepared beforehand and replaced corresponding to an observation target and use.

As for an endoscope apparatus equipped with a detachably attached adapter having an LED illumination device, it is also necessary that the connection parts thereof be detachable from a power supply circuit which supplies electrical power to the LED illumination device from a main power supply.

In the case in which the adapter of the endoscope having such a connection part is connected by mistake during an energizing state in which the main power supply is ON, a rapid energizing of the LED illumination device is performed. On the other hand, in the case in which the adapter is disconnected during energizing the LED illumination device, the energizing will be rapidly stopped.

In general, an endoscope apparatus currently used industrially or medically is equipped with a long insertion part which is inserted into a lumen. Moreover, in such an endoscope apparatus, in order to illuminate the target for observation in a lumen and to make observation and image pick-up easy, there is an illumination device at the tip end of the insertion part.

In recent years, an illumination device having a light emitting diode (which is referred as an "LED", hereinafter) is proposed. Moreover, for example, an endoscope having a plurality of adapters, each of which is detachably attached to the tip end of the insertion part, and is equipped with an LED illumination device and a separate optical system, is proposed. This endoscope is constituted so that an optimal adapter can be selected from a plurality of kinds of adapters prepared beforehand and exchanged corresponding to an observation target and use. Such an endoscope necessitates a connecting constitution for supplying electrical power, between the adapter having an LED illuminating device and the insertion part, and hence a constitution in which a hard electrode is connected to an extensible spring, or a mechanical constitution such as one which is composed of a male connector and a female connector to be connected to each other is used. For example, Japanese Unexamined Patent Application, First Publication Number H10-328131 discloses the above endoscope.

As an exemplification of the adapter having an LED illuminating device which is exchangeably used, for example, adapters each of which observation direction is different, such as one for direct-vision and one for side-view, or an adapter constituted so as to be able to perform various measurements of the observation environment other than image, such as temperature and pressure and the like, can be exemplified. Moreover, in order to be able to select the optimal adapter corresponding to observation targets and purpose, many kinds of adapters of which angular field of view and depth are different from each other, are prepared.

SUMMARY OF THE INVENTION

The endoscope apparatus of the present invention includes a light emitting diode provided on a tip end of an insertion part, and an electrical power supplying circuit of the light emitting diode which is detachably connected to a main power supply, wherein the electrical power supplying circuit has an energizing controlling device of the light emitting diode, which operates upon being connected and disconnected to the main power supply.

The endoscope apparatus of the present invention includes a tip end member provided detachably on a tip end of an insertion part, and an electrical instrument provided on the tip end member, wherein an elastic member made of an anisotropic conductor is provided between the first electrode formed on the tip end member and the second electrode formed on a counterpart member to which the tip end member is detachably attached.

BRIEF DESCRIPTION OF THE DRAWINGS

FIG. 1A is a principal part sectional view showing the example of the tip part of an insertion part, FIG. 1B is an exploded perspective view showing the electrode board of FIG. 1A, and FIG. 1C is an exploded perspective view showing an electrode board and electric conductive rubber from the back end side.

FIG. 5A is a state before storing the main part of the endoscope in a case, and FIG. 5B is a state in which the main part of endoscope apparatus is stored in the case.

FIG. 9A is an exploded perspective view, and FIG. 9B is a perspective diagram showing an assembly completion state.

FIG. 14A is a principal part sectional view showing the tip end part of the insertion part.

FIG. 14B is an exploded perspective view showing the state where the first substrate, an electric conductive rubber and the second substrate are seen from the back end side.

FIG. 14C is an exploded perspective view showing the state where the first substrate, an electric conductive rubber, and the second substrate are seen from the tip end side.

FIG. 14D is a perspective view showing another example of electric conductive rubber.

FIG. 15A shows the state before storing the main part of an endoscope in a case.

FIG. 15B shows the state where the main part of the endoscope apparatus was stored in the case.

FIG. 17A shows a single state of the first substrate.

FIG. 17B shows a state of assembling the first substrate, an electric conductive rubber, and an electric wire.

FIG. 17C shows the state of assembling an LED holding part, a connection ring, and an LED presser.

FIG. 17D shows a state of attaching an outer frame component and an LED substrate to the assembly article of FIG. 17C.

FIG. 17E is a perspective view showing an assembled state.

FIG. 19A shows a state before storing the main part of an endoscope in a storage part.

FIG. 19B shows the state of storing the main part of endoscope apparatus in a case with a storage part.

FIG. 20A shows a tip end part of the insertion part.

FIG. 20B is a figure showing the opposite side of the second substrate shown in FIG. 20A.

FIG. 24A is an exploded perspective view of the principal part.

FIG. 24B is a sectional view of the principal part.

FIG. 25A is a principal part sectional view showing the adapter for side viewing.

FIG. 25B is an exploded perspective view showing a state where the first substrate and electric conductive rubber were seen from the tip end side.

FIG. 26A is an exploded diagram view of an LED substrate.

FIG. 26B is a perspective view showing an assembled state.

FIG. 29A is a perspective view showing an adapter for side viewing constituted so that the tip end member is detachably attached.

FIG. 29B is an exploded diagram view.

DETAILED DESCRIPTION OF THE INVENTION

Hereafter, an embodiment of the endoscope apparatus of the present invention will be explained with reference to drawings.

First Embodiment

The first embodiment of the present invention will be explained based on FIGS. 1A to 1C, 5A, and 5B.

Figure 5A:
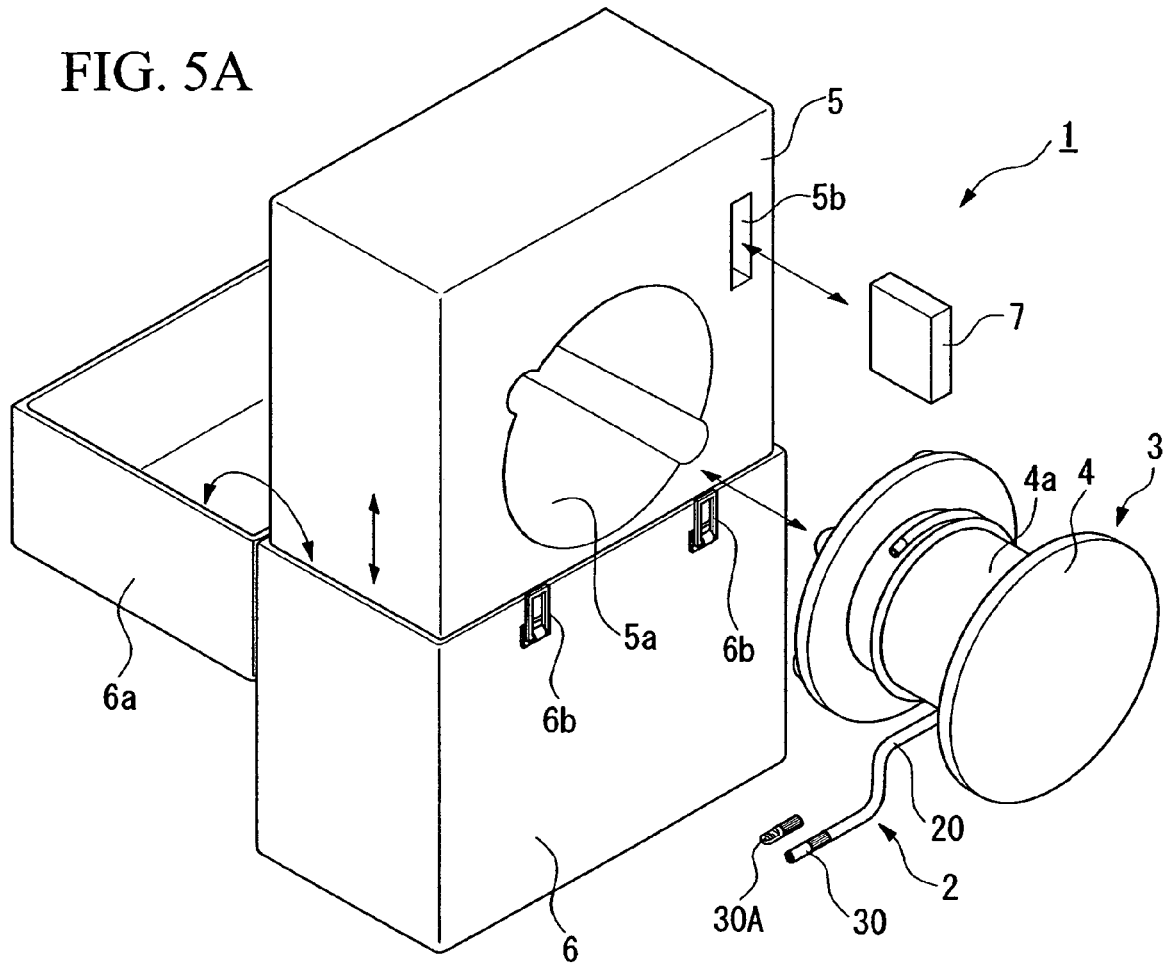
FIGS. 5A and 5B are appearance perspective views showing the entire endoscope apparatus.
Figure 5B:
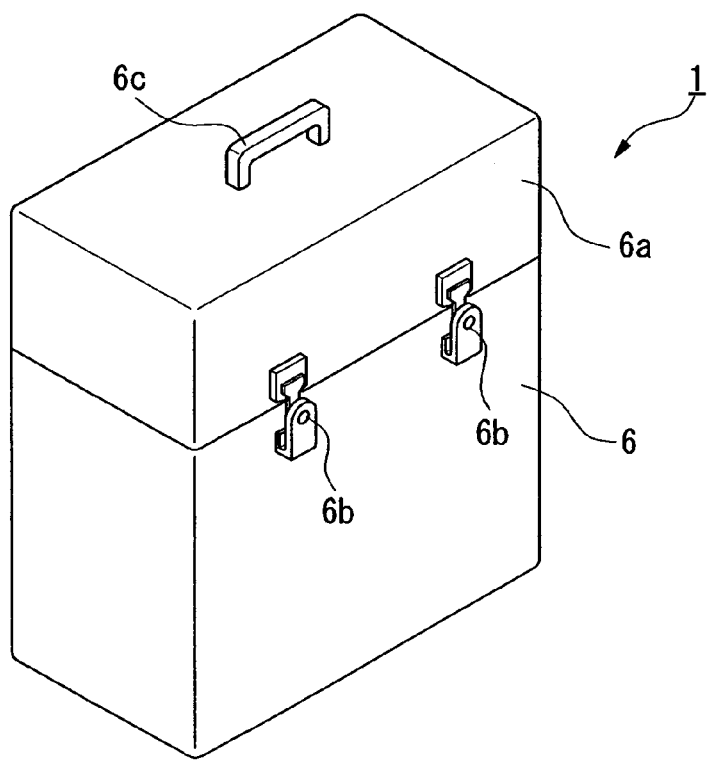

FIGS. 5A and 5B are appearance perspective views showing an entire endoscope apparatus of this embodiment, FIG. 5A shows a state before storing the main part of the endoscope apparatus in a case, and FIG. 5B shows a state where the main part of endoscope apparatus is stored in the case.

This endoscope apparatus 1 is mainly composed of a main body 3 of an endoscope equipped with a long and fine insertion part 2, and a drum part 4 which reels in and stores the insertion part 2 of the main body 3 of the endoscope apparatus.

The main body 3 of an endoscope is inserted into a recess accommodating portion 5a of an accommodating part 5, in a state in which the insertion part 2 is reeled up around the drum part 4, and held there. Thus, the main body 3 of an endoscope as well as the accommodating part 5 is contained in a case 6, and stored and carried in this state. It should be noted that in the drawings the reference numeral 5b denotes an accommodating recess of an adapter case 7, the reference numeral 6a denotes an opening-and-closing lid attached to a case 6 by way of a hinge, the reference numeral 6b denotes a tip, and the reference numeral 6c denotes a handle, respectively.

The drum part 4 is, for example, a bobbin form which is composed of an insertion part reeling part 4a having a cylindrical shape on which the insertion part 2 is reeled up (refer to FIGS. 5A and 5B), and a pair of disk-like flanges one of which is attached to the upper side and the other to the lower side of the insertion part reeling portion 4a.

The drum part 4 is equipped with an image display means, such as an LCD monitor (not shown in the drawings) arranged at appropriate places (for example, flange etc.). Furthermore, in the inside of the insertion part reeling portion 4a, a battery accommodating part (not shown in the drawings) which accommodates a battery for supplying electrical power, and a cylinder accommodating part (not shown in the drawings) which accommodates a cylinder filled up with a working fluid of a fluid pressure actuator FA mentioned later, and a control part which performs various control, are formed. It should be noted that, as the working fluid which is used in a state of being filled in a cylinder, for example, nonflammable gas, such as carbon dioxide, chlorofluorocarbon, nitrogen, helium, argon, and nitrogen, and the like, can be exemplified.

Moreover, a remote controller (not shown in the drawings) which is equipped with a joystick and the like for performing a bending operation of the insertion part 2 mentioned later, etc., is connected to the drum part fourthrough an operation cable.

Figure 2:
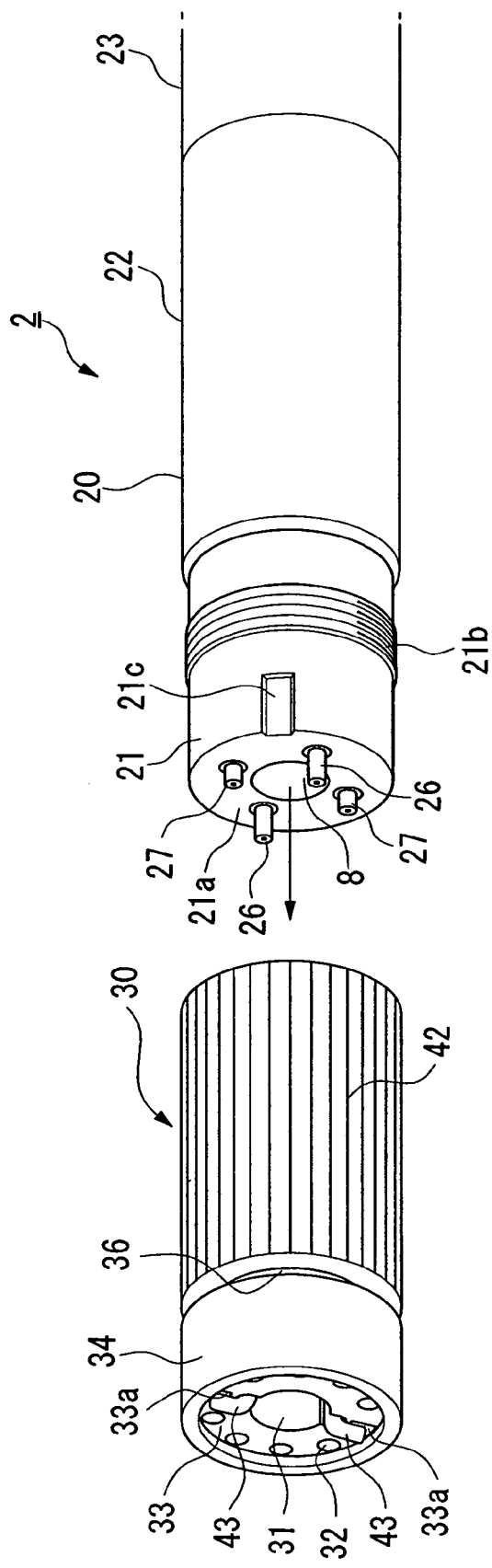
FIG. 2 is a perspective view showing an outline of a tip part of the insertion part of the endoscope apparatus shown in FIGS. 1A to 1C.

As shown in FIG. 2, the insertion part 2 of the main body 3 of an endoscope is constituted from, sequentially from the tip end part inserted into a lumen for observation, an adapter 30 and a flexible tube part 20, each of which is detachably attached to each other.

The adapter 30 is a tip end element which is equipped with an electric apparatus of LED illuminating device 32 and the like, and is detachably attached to the tip end of the insertion part 2. Moreover, a counterpart element to which the adapter 30 is detachably attached serves as a tip end hard part 21 formed on the tip end of the flexible tube part 20. The flexible tube part 20 is composed of the above tip end hard part 21, the bending part 22 for turning the tip end surface of the adapter 30 in the desired observation direction, and a flexible element 23 being flexible and long, which is connected thereto. The bending part 22 is provided on a position slightly behind of the tip end hard part 21, and is equipped with two or more of fluid pressure actuators FA for the use of a bending operation, for example, as explained later based on FIG. 4.

Moreover, on the tip end surface 21a of the tip end hard part 21, two pairs of electrodes, each of which has a projection height from each other, are projected, so that each of these electrodes is connected or disconnected to each of the counterpart electrodes at different time when the adapter 30 is attached or detached to constitute an energizing controlling device.

Figure 3:
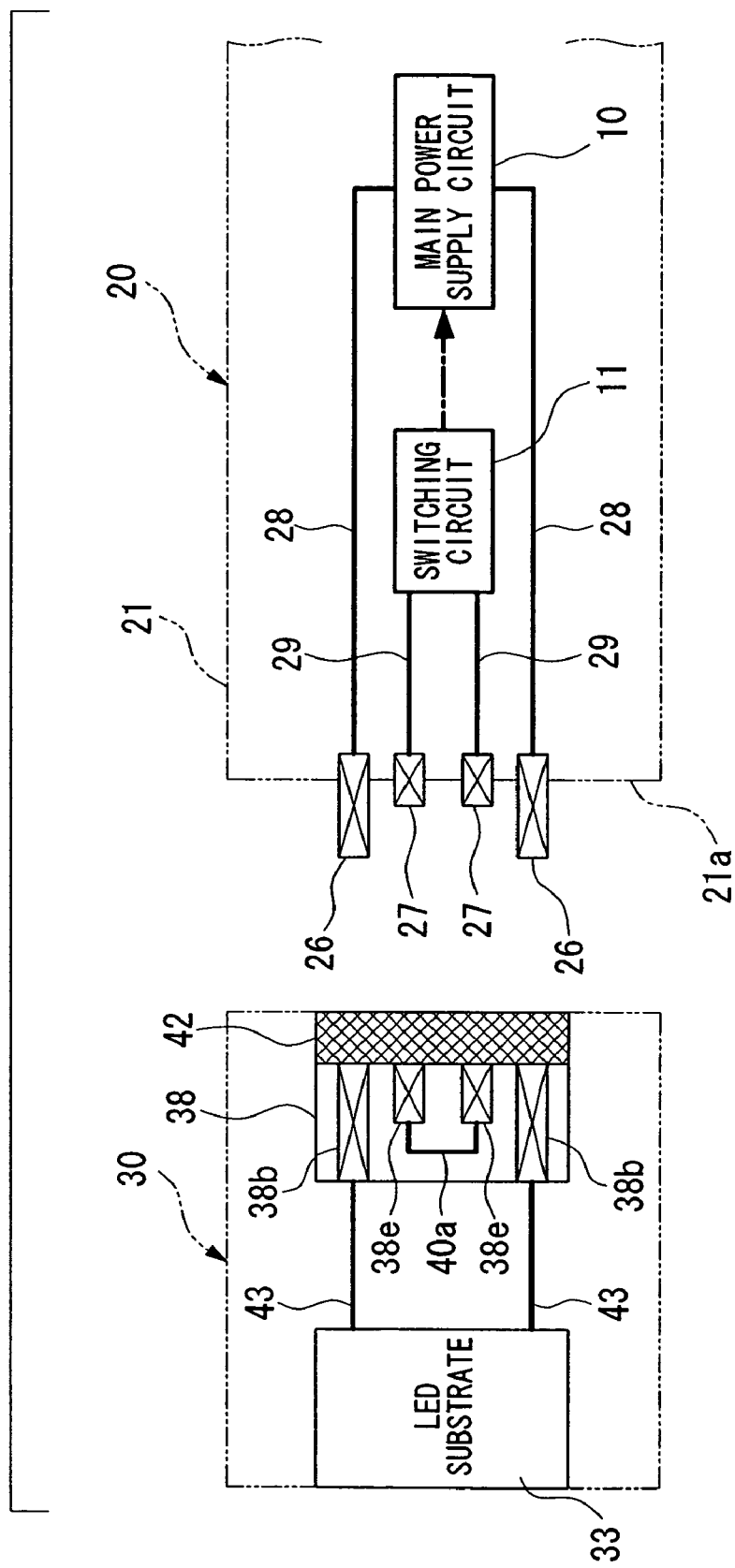
FIG. 3 is a power supply distribution diagram of an insertion part shown in FIGS. 1A-1C, and 2.

One main electrode (the first electrode) 26 is an electrode having a large projection height, which comes into contact formerly in attaching operation, and which loses contact later in detaching operation as shown in FIG. 3. These main electrodes 26 are electrically connected to an electric wire 28 passing through the inside of the insertion part 2, and these main electrodes 26 are connected to the main power supply circuit 10 in the drum part fourthrough the electric wire 28. The main power supply circuit 10 is for supplying electrical power to the LED illuminating device 32 formed in the adapter 30 from a power supply, such as a battery, and is equipped with a relay (switch), which is not shown, for performing ON/OFF operation of energizing. In this case, because the tip end hard part 21 is a metallic member, such as one of a stainless steel, by covering the peripheral surface of the main electrode 26, which is formed into a columnar shape, such as a cylinder, a prism, a hollow cylinder, and the like, with an insulating member (not shown in the drawings), the main electrode 26 can be energized, in the case in which at least a portion of the tip end surface comes into contact with the electrode on the adapter 20 side.

The switch electrode (the second electrode) 27 on the other side is an electrode having a projected smaller than that of the above main electrode 26, such that the switch electrode 27 comes into contact later in attaching operation, and the switch electrode 27 loses contact formerly in detaching operation.

The switch electrode 27 is electrically connected to an electric wire 29 passing through the inside of the insertion part 2, and the switch electrode 27 is connected to a switching circuit 11 through this electric wire 29. The switching circuit 11 has a switch function for making the main power supply circuit 10 be ON, when a gap between a pair of switch electrodes 27 is in conductive state, thereby enabling energizing to the adapter 30 from the main power supply circuit 10. In other words, when the gap between the switch electrodes 27 is turned on, thereby forming a closed circuit on the switch circuit 11, such that the relay of the main power supply circuit 10 will operate and it will be set to ON by the current which flows through the closed circuit, as a result, it becomes possible to energize from the main power supply circuit10 to the adapter 30.

The adapter 30 is composed of an observation window 31 which is formed, for example at the center of the tip end surface, and a plurality of LED illuminating devices (electric instrument) 32 arranged the observation window 31.

The plurality of LED illuminating devices 32 are arranged in a circumference direction on one surface (front surface) of the LED substrate 33 which is formed into a toroidal shape having a penetrated hole in the center of the disk substrate, The LED substrate 33 is, as shown in FIGS. 1 and 2, inserted into a front end of an outer frame member 34 which is formed into approximately a hollow cylinder, and of which positioning is performed by abutting the front end surface, on which the plurality of LED illuminating devices 32 are provided, of the LED substrate 33 to a hook part 34a formed by bending the front end of the outer frame member 34 inside.

To the outer frame member 34 into which the LED substrate 33 is inserted, an LED holding part 35 and an LED presser 36 are inserted from an opening formed at a back end side.

An object lens group 37 which serves as an optical lens system is provided to a space part 36a formed along the axial center of the LED presser 36. In an example shown in the drawings, the object lens group 37 is constituted from the first lens 37a, a spacer 37b, the second lens 37c, a spacer 37d, an iris diaphragm 37e, and the third lens 37f, each of which is arranged in this order sequentially from the tip end surface, on which an opening is formed, along the direction of an axis.

An electrode substrate 38 and an elastic member (hereafter referred as an "electric conductive rubber") 42 having different direction conductivity are inserted sequentially from the tip end surface side at the perimeter side, into an inner cylinder part 36b of the LED presser 36 which forms the space part 36a.

Figure 1A:
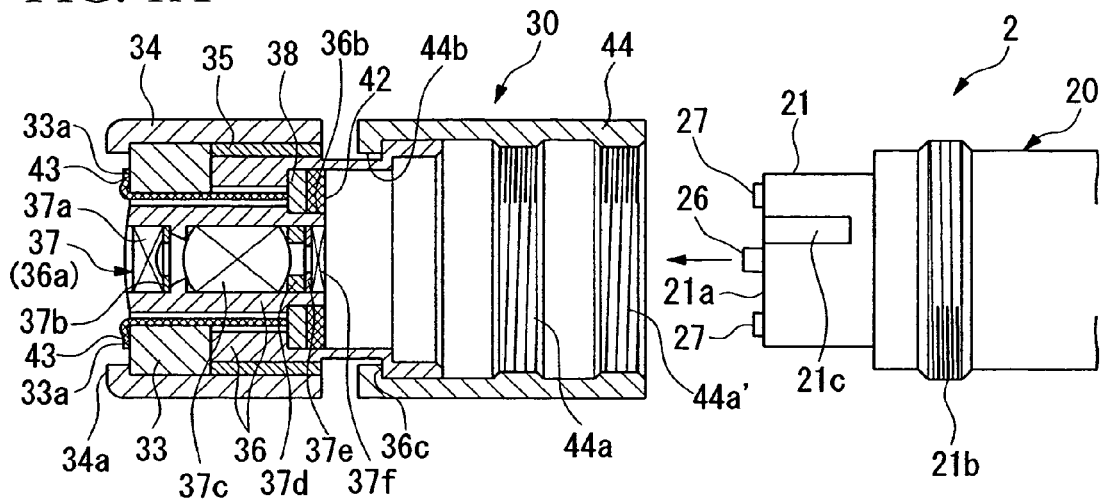
FIGS. 1A to 1C show the first embodiment of the endoscope apparatus of the present invention.
Figure 1B:
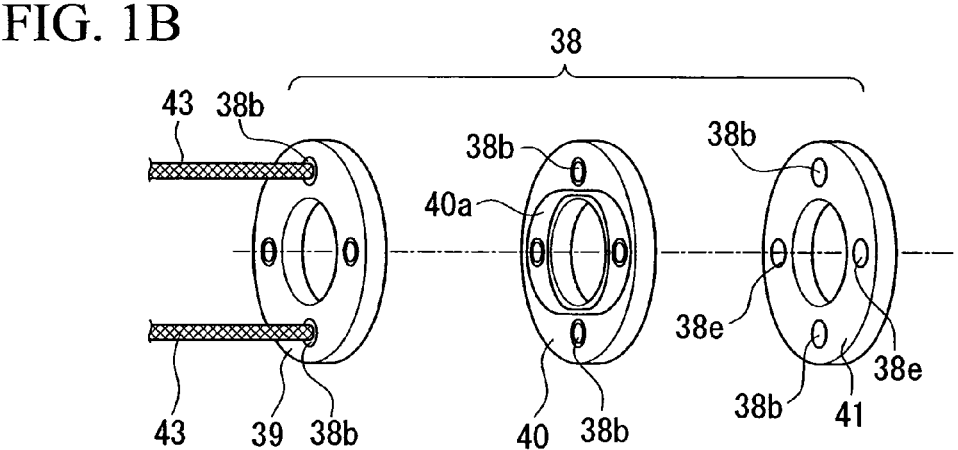
Figure 1C:
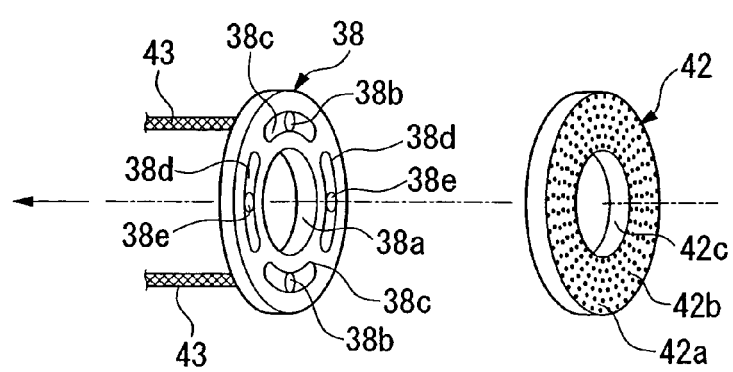

The electrode substrate 38 is a laminate which is composed of three sheets, the first substrate 39, the second substrate 40, and the third substrate 41, as shown, for example in FIG. 1B. The electrode substrate 38 has, as shown in FIG. 1C, a toroidal shape which is formed by penetrating a penetrated hole 38a at the center of a disk resin substrate (it is referred as a "disk" hereinafter), thereby making positioning easy, and a pair of through holes 38b are formed outside of the penetrated hole 38a, each of the pair of through holes 38b is formed on upper and lower sides of the resin substrate with respect to the penetrated hole 38a, and the inner surface of each of the pair of through holes 38b is coated with a conductive material. To these through holes 38b, electric wires 43 for supplying electric power for the LED illuminating device 32 to the LED substrate 33 are electrically connected respectively, by soldering and the like.

Moreover, on the back end surface of the electrode substrate 38, a pair of main electrode patterns 38c consisting of an upper one and a lower one, and a pair of switch electrode patterns 38d consisting of a left one and a right one, are provided independently, respectively. These electrode patterns 38c are electrically connected to a conductive material which covers the inner surface of the through hole 38, respectively, and each of the pair of switch electrode patterns 38d forms an electrical connection at the substrate inside.

One of the main electrode pattern 38c is independent from every pair of through holes 38b, in other words, each of the pair of main electrode patterns 38c is isolated from each other, so that short-circuiting is avoided, and each of which is formed to be a circular arc shape. Moreover, the other switch electrode pattern 38d is independent from every pair of through holes 38e, each of the switch electrode pattern 38d is formed to be a circular arc shape. These through holes 38e in this case are not penetrating through the electrode substrate 38, each of these through holes 38 is electrically connected to each other through a conductive material inside the substrate.

The circular main electrode pattern 38c and the switch electrode pattern 38d mentioned in the above can be omitted, and it may be possible to provide simply an electrode composed of a conductive member which is exposed to both ends of the through hole 38b and one end part of the through hole 38e.

It should be noted that the other end of the electric wire 43 mentioned in the above passes along the electric wire passage formed between the LED board 33 and the LED presser 36, and is connected to the electrode part 33a provided on the tip end surface of the LED substrate 33.

Among the three substrates 39, 40, and 41 which constitute the electrode substrate 38 mentioned above, the first substrate 39 which is laminated as a surface layer at the LED substrate 33 side (front end surface) is one on which a pair of electric wires 43 are connected to a pair of the through holes 38b including an upper one and a lower one, respectively. Moreover, the second substrate 40 which is laminated as a middle layer is one which is unified with a pair of through holes 38b composed of an upper through hole and a lower through hole, by an electric conductive material, and is equipped with a conductive pattern part 40a electrically connected to a pair of through holes 38e composed of a right one and a left one. Furthermore, the third substrate 41 which serves as an opposite-side surface layer (back end surface) of the LED substrate 33 and the surface coat by the side of opposite (back end side) is equipped with a pair of through holes 38b composed of an upper one and a lower one, each of which has the main electrode pattern, and a pair of through holes 38e composed of a right one and a left one each of which of has the switch electrode pattern 38d.

An electric conductive rubber 42 is composed of many conductive members 42b arranged in dots on the elastic body 42a being an insulator, and the electric conductive rubber 42 is, for example, referred as an anisotropic rubber.

The electric conductive rubber 42 is one constituted from the elastic body 42a which is made of a silicone rubber sheet or the like, and conductive members 42b such as metal particles or nickel particles on which gold plating is deposited, or the like, arranged in a thickness direction of the elastic body 42a.

Therefore, by pressing lightly the electric conductive rubber 42 in the thickness direction thereof, the electrical conductivity between the conductive members 42b of which density is increased, and a good electrical connection in the thickness direction thereof can be attained. However, because the elastic body 42a is an insulating member, the conductive rubber 42 has insulation properties except in the thickness direction thereof (for example, the direction of a circumference). In this case, each of the conductive members 42b arranged in dots (the portions exposed to both surfaces are dot-like) is isolated by insulating members from each other, thereby forming a non-conductive and independent state.

Moreover, similar to the above electrode substrate 38, the conductive rubber 42 is formed in a toroidal shape with a penetration hole 42c at the center thereof, thereby making positioning easy.

Although the electric conductive rubber 42 of a dot type on which the conductive members 42b in the shape of dots were arranged was adopted in the above embodiment, it is also possible to use, for example, a stripe type conductive rubber.

The stripe type conductive rubber is one constituted from an elastic body made of insulator and conductive members which are disposed in a thickness direction of the elastic body are arranged in the shape of a stripe on the elastic body. In this case, each of the conductive members which are arranged in a stripe shape (the portions exposed to both surfaces and to each of cross-sections have a stripe shape, respectively) is isolated from each other by an insulating member, thereby forming a non-conductive and independent state.

It should be noted that the arrangement direction and the arrangement form (for example, parallel arrangement and the like) of the conductive members having a stripe shape are not particularly limited, as long as each of the conductive members is isolated from each other.

A connecting ring 44 is disposed rotatably at the perimeter back end side of an LED presser 36. The connecting ring 44 is substantially a cylindrical member having an inner thread part 44a on the inner surface, which engages with an outer thread part 21b formed on the perimeter of an insertion part 2b mentioned later.

The LED presser 36 penetrates the connecting ring 44, and a step part 36c of the LED presser 36 engages with an engage part 44b formed on the tip end of the connecting ring 44 to prevent the connecting ring 44 from being dropped out in an axial direction of the connecting ring 44.

It should be noted that an inner thread part 44a', which prevents the connecting ring 44 from being dropped out of the insertion part 2, is formed on the back end side of the inner surface of the connecting ring 44.

Thus, the conductive rubber 42 is exposed to the inside of the adapter 30 having the LED illuminating device 32 at the tip end surface thereof, through the opening at the back end side of the connecting ring 44 and the LED presser 36.

In other words, the conductive rubber 42 is disposed such that the conductive rubber 42 is exposed to the inner surface of the adapter 30 which faces to a tip end surface 21a of the insertion part 2 in a connected state.

It should be noted that, such an adapter 30 includes, for example, an adapter 30A for side viewing which is equipped with an observation window or an LED illuminating on the side (circumference side) and an adapter of which object lens group 37 constitution and optical specification differ, in addition to the above one for a direct-vision which is equipped with the observation window 31 and the LED illuminating device 32 on the tip end surface.

In the tip end hard part 21 of the insertion part 2, in order to pick up the image captured from the observation window 31 of the adapter 30 through the object lens group 37, for example, a CCD 8 is installed as an observation device. The CCD 8 is connected to the main body 3 of the endoscope through a cable 8a passing through an inner space of the insertion part 2, and the CCD 8 transmits image signals picked up while receiving electrical power supplied from the inside of the drum part 4. It should be noted that the above observation device is not limited to CCD 8, and may be a C-MOS, an image guide fiber, or the like.

Figure 4:
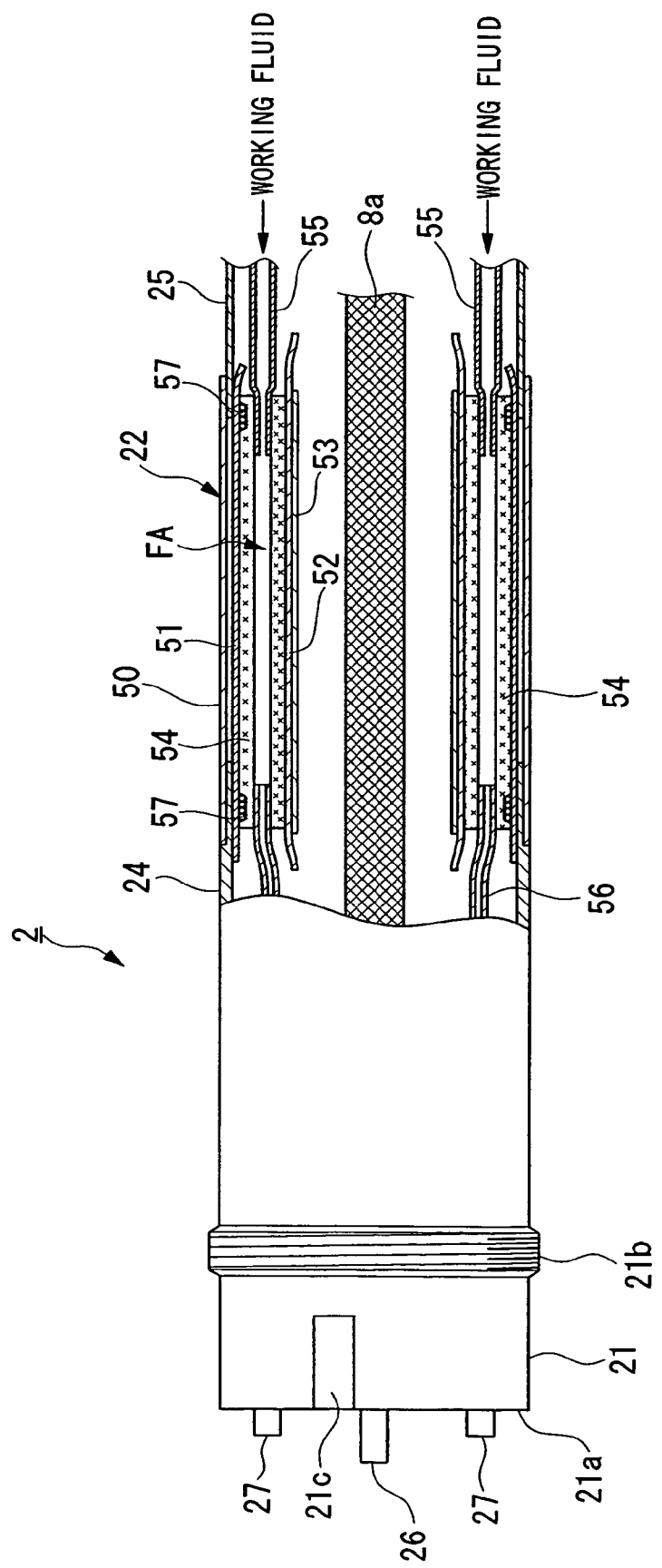
FIG. 4 is a principal part sectional view showing an example using a fluid actuator of the bent side at the tip end of the insertion part.

A fluid actuator FA is disposed between the front cap 24 connected to the tip end hard part 21 and the back cap 25 connected to the flexible member 23, as shown in FIG. 4.

The fluid actuator FA is constituted from an outer coil pipe 50, an outer tube 51, an inner tube 52, an inner coil pipe 53, and a multi-lumen tube 5fourthe outer coil pipe 50 and the outer tube 51 are connected to the front cap 24 and the back cap 25, respectively, such that each of the front cap 24 and the back cap 25 is interposed between the outer coil pipe 50 and the outer tube 51 at both ends of the outer coil pipe 50 and the outer tube 51.

The inner tube 52 and the inner coil pipe 53 are inserted inside the outer coil pipe 50 and the outer tube 51, and the multi-lumen tube 54 is disposed between the inner tube 52 and the outer tube 51.

The multi-lumen tube 54 is a member having a substantially circular cross-section, which is made of a flexible silicone material, and is equipped with a plurality of (for example, at four places at a 90-degree pitch) air chambers each of which is formed at an equivalent pitch in a direction of the circumference.

As for the multi-lumen tube 54, one end of the air chamber is connected to a working fluid feed pipe 55, and the other end is connected to the connection tube 56. The working fluid feed pipe 55 at one side is connected to the cylinder of the main body 3 of the endoscope so as to supply the working fluid to the air chamber of the multi-lumen tube 54. It should be noted that, the other end of the connection tube 56 is connected to a pressure sensing means (which is not shown in the drawings) which detects, for example, the pressure of the working fluid to perform feedback control.

The outer coil pipe 50 and the inner coil pipe 53 in the above are tubular members which are, for example, made of stainless steel which curves easily. Moreover, the outer tube 51 and the inner tube 52 are thin tubes which are, for example, made of fluoride, and which prevent the multi-lumen tube 54 from being inserted between the lines of the outer coil pipe 50 and the inner coil pipe 53, thereby being broken. It should be noted that, the reference numeral 57 in the drawings denotes a wound yarn for fixation.

Because the fluid actuator FA constituted in the above bends at a stretched side where the multi-lumen tube 54 is expanded by the supplied working fluid, what is necessary for bending the fluid actuator FA is substantially to supply the working fluid to the multi-lumen tube 54 at an opposite side of the direction (the direction of 180 degrees) of the desired curve, thereby making it expand.

In addition, of course the means for bending the bending part 22 is not limited to the above fluid actuator FA, for example, other well-known means, such as a wire type, or the like can be used.

In the endoscope apparatus 1 with such a constitution, after selecting a desired adapter 30 and inserting the tip end of the insertion part 2 into the back end side opening of the connecting ring 44 the connecting ring 44 is rotated to be connected to the insertion part 2.

In this moment, at first, the thread part 21b engages with the inner thread part 44a' of the connection ring 44 outside the tip end hard part 21, and if the rotating of the connection ring 44 is kept on further, the outer thread part 21b transits the inner thread part 44a' to progress to the tip end side, thereby being released from being engaged with the inner thread part 44a'. As a result, the outer thread part 21b reaches a space between a pair of the inner thread parts 44a and 44a' having a predetermined interval to be free, and hence the inner thread part 44a' abuts on the outer thread part 21b, thereby functioning as a stop which prevents the adapter 30 from dropping out of the flexible tube part 20.

In the case of rotating the connecting ring 44 further, with squeezing the insertion part 2 therein, from such a space where the dropping out is prevented, at this time the outer thread part 21b is screwed with the inner thread part 44a, and hence the adapter 30 is connected to the insertion part 2 in a state where the adapter is fixed to a predetermined position with respect to the tip end of the insertion part 2.

It should be noted that the reference numeral 21c in the figure denotes a concave groove part which is formed for positioning in a direction of circumference, which performs the positioning by engaging with a convex part, which is not shown in the drawing, and is formed on an inner circumference surface of the LED presser.

In the case in which the adapter 30 is connected to the insertion part 2 in the predetermined position mentioned above, the main electrode 26 which projects from the tip end surface 21a at first abuts on the electric conductive rubber 42, thereby pressing the electric conductive rubber 42 in the direction of the tip end part. Therefore, the electric conductive rubber 42, which is made of an elastic body and interposed by the electrode substrate 38 of which movement to the tip end part side is prevented by the LED presser 36, is compressed, such that the density of the electrical conductive members 42b which are arranged in a thickness direction of the electrical conductive rubber 42 is increased, thereby improving the electrical conductivity to form an energizing state.

However, in this state, because the switching electrode 27 of which projecting height is small has not reached the electric conductive rubber 42, the two switch electrodes 27 are in a nonconductive state, and the switching circuit 11 does not operate the relay of the main power supply circuit 10.

Thereafter, because the electric conductive rubber 42 is compressed to be deformed, the switching electrode 27 comes into contact with the electric conductive rubber 42 slightly later than the main electrode 26, and the gap between the two switching electrodes 27 becomes electrically conductive through the electric conductive rubber 42 and the electric conductive pattern part 40a of the electrode substrate 38. Therefore, because a closed circuit which is electrically conductive to the switching circuit 11 is formed, the relay of the main power supply circuit 10 operates by the switch function of the switching circuit 11, it is set to ON, and energizing to the LED substrate 33 from the main power supply is started slowly.

Moreover, in case in which the adapter 30 is removed from the insertion part 2, contrary to the above procedure, the switching electrode 27 is isolated from the electric conductive rubber 42 first, thereby stopping the energizing to the switch circuit 11. For this reason, because the relay of the main power supply circuit 10 operates to set it to be OFF, and the main electrode 26 is isolated from the electric conductive rubber 42 slightly later, such that the energizing from the main power supply to the LED substrate 33 is stopped slowly.

As mentioned above, because the energizing control device of this embodiment is equipped with the main electrode 26 and the switching electrode 27, each of which having a projection height which is different, such that connecting operation and isolating operation to the counterpart electrical conductive member are performed with time difference upon being attached and detached, by intervening the electric conductive rubber 42 made of an elastic material which is deformed in a direction of attaching and detaching, thereby enabling the switching circuit 11 provided on the side of the switching electrode 27, which has a small projection height and becomes into contact later and loses contact formerly, to be used for operating the relay of the main power supply 10, such that the energizing of the main power supply can be controlled.

Therefore, in attaching and detaching operation, the main electrode 26 and the switching electrode 27 come into contact or lose contact with time difference, and hence energizing suddenly from the main power supply circuit to the LED substrate 33 or stopping energizing suddenly from the main power supply circuit to the LED substrate 33 does not occur, and as a result, a rapid current change does not occur.

That is, because a rapid temperature change on the LED illuminating device 32 caused by a rapid current change does not occur, degradation and breakage generated thereby can be controlled and prevented.

Although the electric conductive rubber 42 is used as an elastic member which deforms in a direction of attaching and detaching in the above embodiment, an elastic member (such as a spring member, e.g., a coil spring, and a rubber) which gives urging force in the projecting direction to the inside of the main electrode 26 and the switching electrode (back end part) can be provided in addition to this or alone.

It should be noted that adopting the electric conductive rubber 42 which is a tabular member is advantageous for reducing the diameter the insertion part 2, in comparison with a constitution of providing an elastic member inside an electrode. Moreover, because the electric conductive rubber 42 is an elastic body, a good adherence can be formed in the contact with the main electrode 26 and the switching electrode 27, and further in the contact with the main electrode pattern 38c and the switching electrode pattern 38 of the main electrode substrate 38, such that it can be made to energize reliably through the electrical conductive rubber 42 of which electrical conductivity is improved.

Second Embodiment

Figure 6:
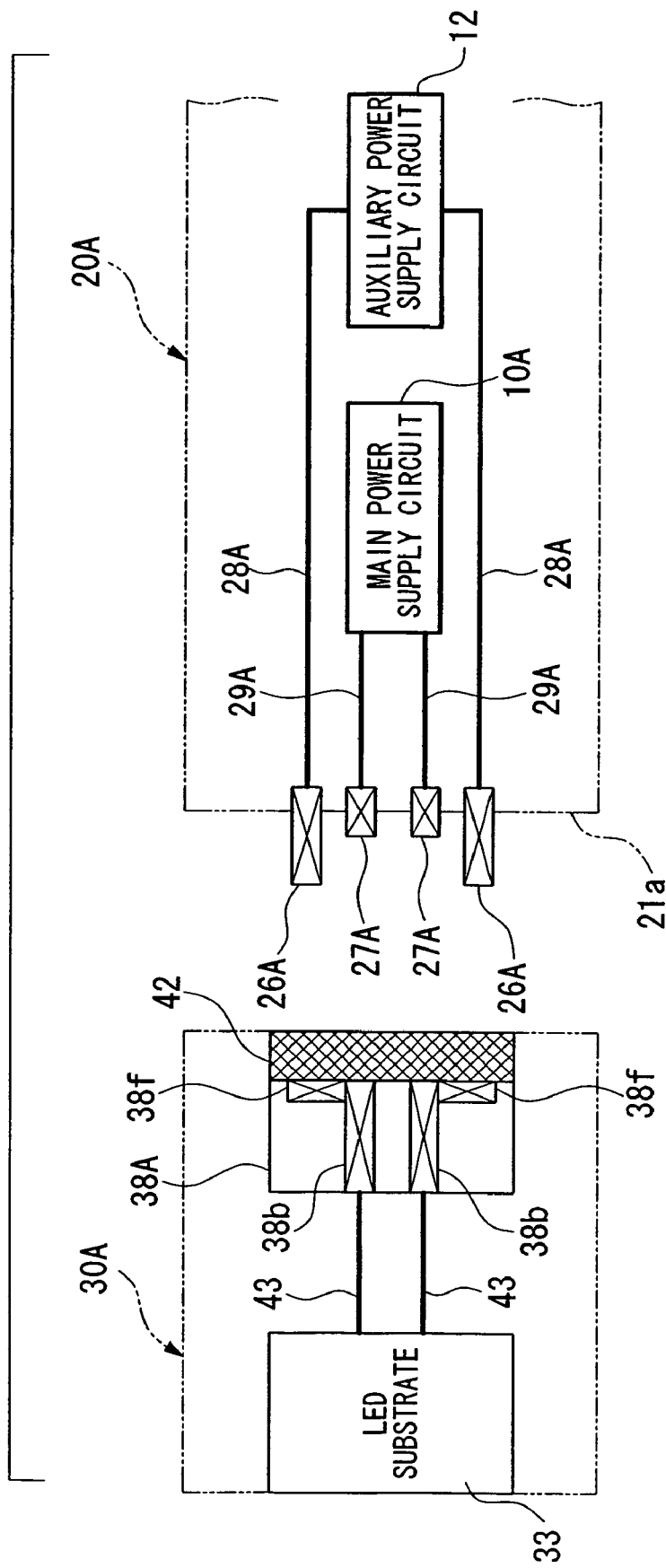
FIG. 6 is a power supply distribution diagram of the insertion part showing the second embodiment of the endoscope apparatus of the present invention.
Figure 7:
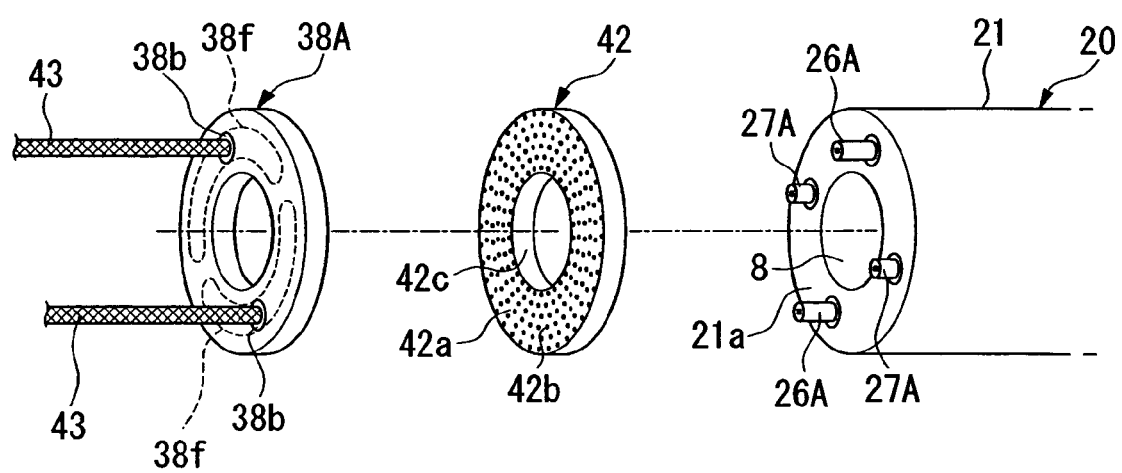
FIG. 7 is an exploded perspective view showing an example of an electrical system of the insertion part shown in FIG. 6.

Next, the second embodiment of the present invention will be explained based on FIGS. 6 and 7. It should be noted that the same reference numerals are given to the corresponding portions in the first embodiment above, and detailed explanation thereof is omitted.

In the energizing control device shown in this embodiment, two pairs of electrodes 27A each of which having a projection height which is different, that is, the main power supply electrode (the second electrode) 27A and the auxiliary power supply electrode (the first electrode) 26A are provided on the tip end surface 21a of the insertion part 2. The projection height of the main power supply electrode 27A on one side is formed to be lower than that of the auxiliary power supply electrode 26A, and the main power supply electrode 27A is connected to the main power supply circuit 10A of which power supply voltage is high (for example, about 12V) through the electric wire 29A. Moreover, the auxiliary power supply electrode 26A on the other side is connected to the auxiliary power supply circuit 12 of which supply voltage is set to be low (for example, about 5V) through the electric wire 28A.

The electrode substrate 38A on the adapter 30 side is equipped with a pair of through holes 38b to which electric wires 43 are connected on the front tip end surface side thereof, and a pair of electrode patters 38f each of which is electrically connected independently from each other, on the back tip end surface side thereof.

It should be noted that, each of the auxiliary power supply electrode 27A and the main power supply electrode 26A comes into contact with each of the electrode patterns 38f, one by one.

By constituting in this way, the auxiliary power supply electrode 26A which projects from the front tip end surface 21a at first comes into contact with the electric conductive rubber 42 and presses the electric conductive rubber 42 in a direction of the tip end part.

For this reason, the electric conductive rubber 42 of the elastic body interposed between the electrode substrates 38 of which movement to the tip end part side is restricted is compressed, thereby increasing the density of the electric conductive members 42b arranged in the thickness direction, such that the conductivity is improved to form an energizing state.

Therefore, an energizing is started at first from the auxiliary power supply circuit 12 of which supply voltage is low to the LED substrate 33. However, in this state, because the main power supply electrode 27A with a small projection height has not reached the electric conductive rubber 42, energizing from the main power supply circuit 10A of which power supply voltage is high to the LED substrate 33 does not occur.

Because the electric conductive rubber 42 is compressed and elastically deformed thereafter, the main power supply electrode 27A comes into contact with the electric conductive rubber 42 slightly later than the auxiliary power supply electrode 26A, thereby starting energizing from the main power supply circuit 10 to the LED substrate 33. Therefore, because energizing from the main power supply with a high voltage is started with a time difference after energizing to the LED substrate 33 from the auxiliary power supply with a low voltage first, rapid of change voltage can be reduced.

In addition, in case of removing the adapter 30 from the insertion part 2, contrary to the above operation, the main power supply electrode 27A is isolated at first from the electric conductive rubber 42, subsequently the auxiliary power supply electrode 26A is isolated from the electric conductive rubber 42, and hence change of voltage in energizing the LED substrate 33 is reduced, thereby preventing the voltage from being rapidly changed.

Thus, because the energizing control device of this embodiment is equipped with the auxiliary power supply electrode 26A and the main power supply electrode 27A, each of which having a projection height which is different, such that connecting operation and isolating operation to the counterpart electrical conductive member are performed with time difference upon being attached and detached, by intervening the electric conductive rubber 42 made of an elastic material which is elastically deformed in a direction of attaching and detaching, the energizing from the main power supply circuit 10A with a high voltage which is connected to the side of the main power supply electrode 27A with a small projection height which comes into contact later and loses contact formerly is started or ended by way of energizing through the auxiliary power supply circuit 12 with a low voltage.

Therefore, energizing suddenly from the main power supply circuit 10A to the LED substrate 33 or stopping energizing suddenly from the main power supply circuit 10A to the LED substrate 33 does not occur, and hence a rapid change of current in the LED illuminating device 32 does not occur.

That is, because a rapid temperature change on the LED illuminating device 32 caused by a rapid current change does not occur, degradation and breakage generated thereby can be controlled and prevented.

Third Embodiment

Figure 8:
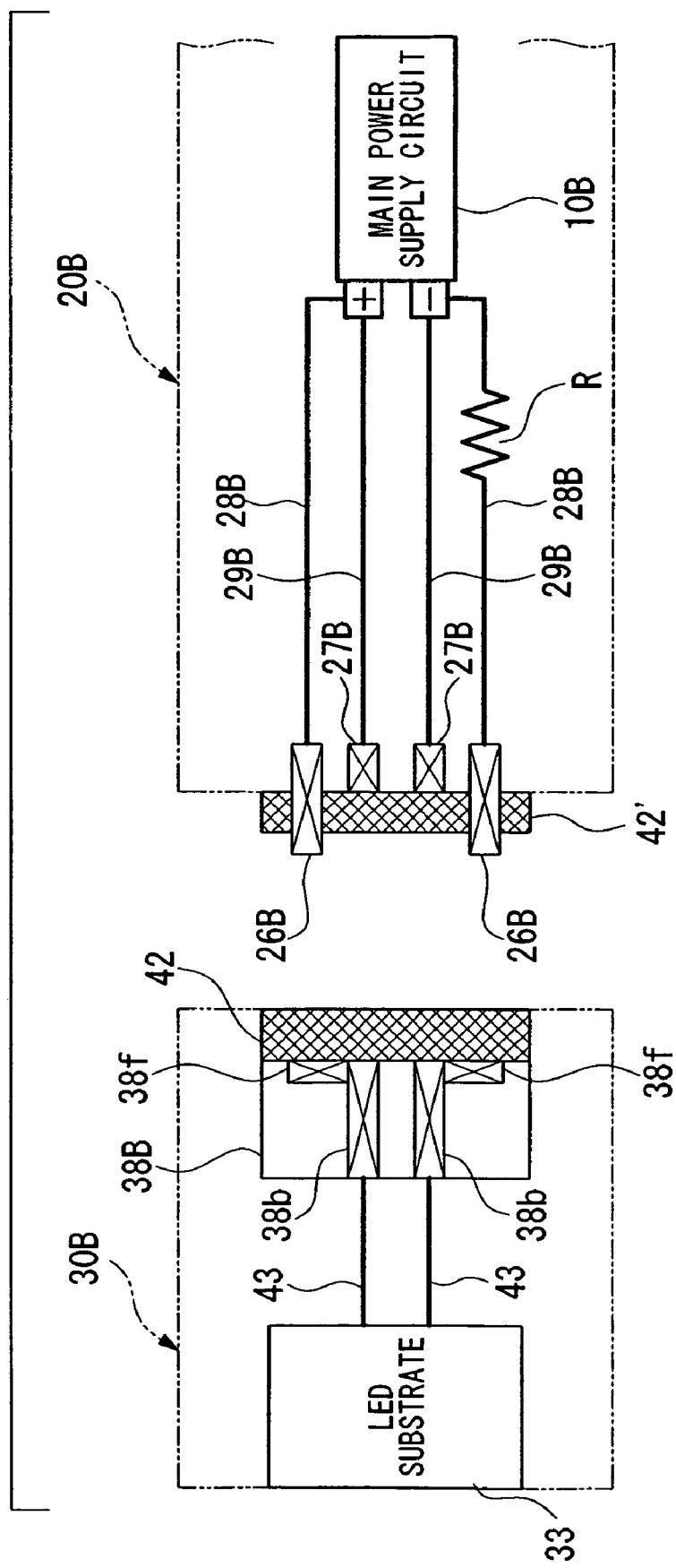
FIG. 8 is a power supply distribution diagram of the insertion part showing the third embodiment of the endoscope apparatus of the present invention.
Figure 9A:
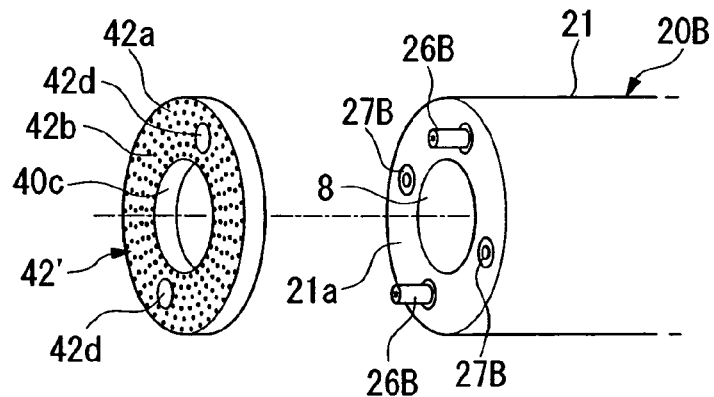
FIGS. 9A and 9B are figures showing an example of a constitution near the tip end side of the insertion part shown in FIG. 8.
Figure 9B:
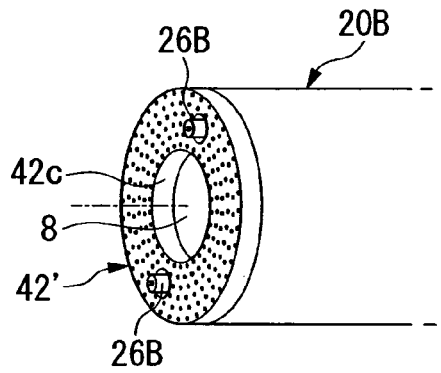

Next, the third embodiment of the present invention will be explained based on FIGS. 8, 9A, and 9B. It should be noted that the same reference numerals are given to the corresponding portions as in each of embodiments mentioned above, and detailed explanation thereof is omitted.

The energizing control device of this embodiment is, similar to the second embodiment mentioned in the above, equipped with two pairs of electrodes each of which having a projection height which is different on the tip end surface 21a of the insertion part 2, that is the main electrodes (the second electrode) 27B and the auxiliary electrodes (the first electrode). The projection height of the main electrode 27B on one side is formed to be less than that of the auxiliary electrode 26B, and the main 27B is formed to project slightly from the tip end surface 21a. Moreover, the height of the auxiliary electrode 26B on the other side is formed to penetrate the electric conductive rubber 42' in its thickness direction and project therefrom. It should be noted that, the auxiliary electrode 26B and the main electrode 27B are connected to the main power supply circuit 10B through the electric wires 28B and 29B, respectively.

Although the electric conductive rubber 42' used here is basically identical to one which is mentioned above, two penetrating holes 42d through which the auxiliary electrode 26B is passed are formed therein. The electric conductive rubber 42' is disposed so as to come into closely contact with the main electrode 27B of which one tip end surface projects from the tip end surface 21a.

Here, in this embodiment, the resistance R is disposed to proper places of the electric wire 28B which connects the auxiliary electrode 26B and the main power supply circuit 10B.

Moreover, the electrode substrate 38B is equipped with two of through holes 38b on the front tip end surface side to which the electric wires 43 are connected, and a pair of the electrode patterns 38f each of which is independently connected to the through holes respectively on the back tip end surface side. It should be noted that to each of the electrode patterns 38f, the auxiliary electrode 27B, and the main electrode 26B come into contact one by one.

Because it is constituted in this way, the auxiliary electrode 26B which projects from the tip end surface of the electric conductive rubber 42' comes into contact with the electric conductive rubber 42 first and presses the electric conductive rubber 42 in a direction of the tip end part. For this reason, the electric conductive rubber 42 which is made of an elastic body and interposed between the electrode board 38B of which movement toward the tip end part is restricted is compressed, thereby making the electric conductive member 42b arranged in the thickness direction high-density, such that conductivity is improved and the energizing state is formed. Therefore, the voltage of a small current value which flows through the resistance R first will be energized from the main power supply circuit 10B to the LED substrate 33. However, in this state, because the electric conductive rubber 42' has not reached to the position where the electric conductive rubber 42' comes into contact with the electric conductive rubber 42, a large current is not applied directly from the main power supply circuit 10B to the LED substrate 33.

Because the electric conductive rubber 42 is compressed by the auxiliary electrode 26B to be elastically deformed thereafter, the electric conductive rubber 42' comes into contact with the electric conductive rubber 42 slightly later than the auxiliary electrode 26B, thereby starting energizing from the main power supply circuit 10B to the LED substrate 33 by way of the electric wires 29B.

Therefore, because a current which will have a usual current value with a time difference is energized from the main power supply circuit 10B, after the small current which flows through the resistance R first is energized from the main power supply circuit 10B to the LED substrate 33, a sudden change of current can be reduced.

Moreover, in the case of detaching the adapter 30B from the insertion part 2, contrary to the operation mentioned above, at first the electric conductive rubber 42' is isolated from the electric conductive rubber 42, subsequently the auxiliary electrode 26B is isolated from the electric conductive rubber 42, and hence the change of the current which is energized to the LED substrate 33 is reduced and the current does not decrease suddenly.

Thus, the auxiliary electrode 26B and the main electrode 27B each of which having a projection height which is different are provided, such that these two electrodes come into contact with and lose contact with the counterpart electric conductive members, respectively, with time difference, upon being attached and detached. In addition, at the portion of connecting the flexible tube part 20B with the adapter 30B, the electric conductive rubber 42 which is made of an elastic material and is elastically deformed in the attaching and detaching direction is disposed. As a result, at a side of the main electrode 27B having a small projection height, which comes into contact later and loses contact formerly with the counterpart member, that is, the electric conductive rubber 42, the energizing from the main power supply circuit 10B which is connected directly without disposing the resistance R therein is started or ended by way of the energizing through the auxiliary electrode 26B which can reduce the current value by the resistance R disposed in the electric wire 28B.

Therefore, it does not occur to energize a high voltage (large current) suddenly from the main power supply circuit 10B to the LED substrate 33 or to stop suddenly a current which is energized from the main power supply circuit 10B to the LED substrate 33, and hence a rapid current change on the LED illuminating device 32 does not occur. That is, because a rapid temperature change on the LED illuminating device 32 by a rapid current change does not occur, the degradation and breakage caused thereby can be controlled and prevented.

Fourth Embodiment

Figure 10:
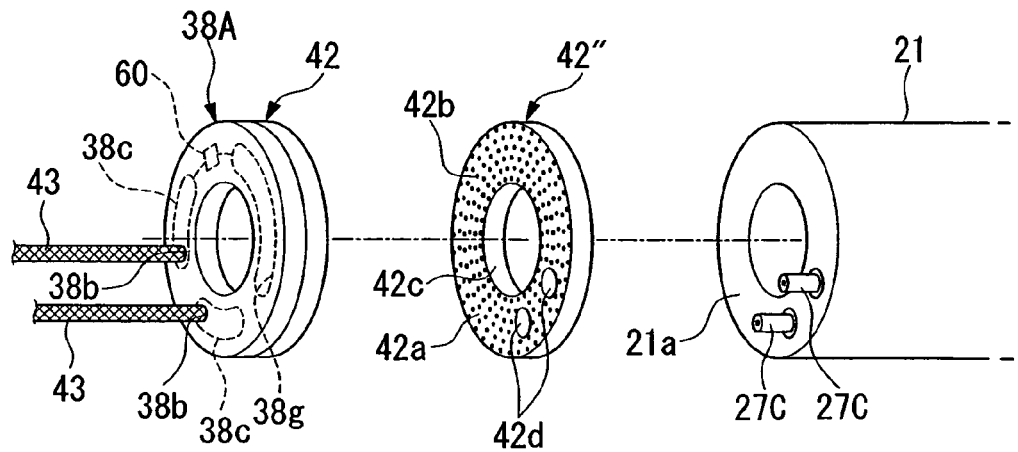
FIG. 10 is a figure showing an example of a power supply system of the insertion part which shows the fourth embodiment of the endoscope apparatus of the present invention.

Next, the fourth embodiment of the present invention will be explained based on FIGS. 10 to 12. It should be noted that the same reference numerals are given to the corresponding portions as in each of embodiments mentioned above, and the detailed explanation thereof is omitted.

The energizing control device of this embodiment is equipped with the switching element 60 as an energizing control device. The switching element 60 is, as shown in FIG. 12, for example, equipped with an energizing delay function which makes the actual energizing start at a timing when a predetermined time t1 is passed from the start of energizing (that is, the start of energizing is delayed), and the switching element 60 is disposed to the electrode substrate 38A, which is disposed as well as the LED illuminating device 32 in the adapter 30 of the tip end part side which is isolated from the insertion part 2.

Figure 11:
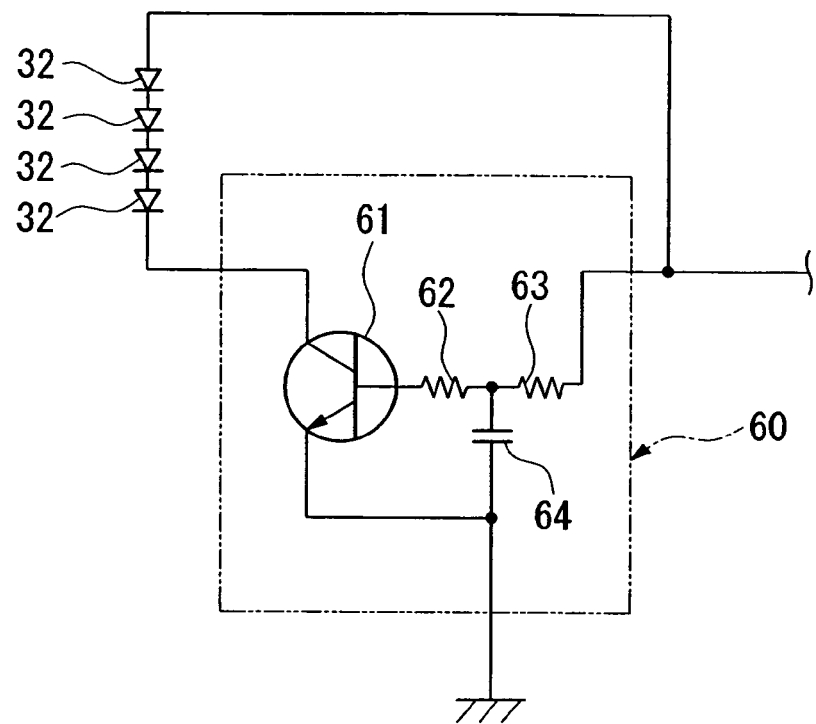
FIG. 11 is a circuit diagram showing an example of the switching element shown in FIG. 10.
Figure 12:
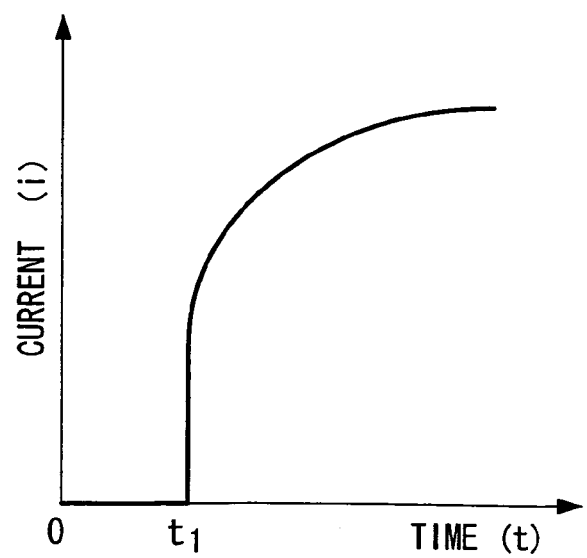
FIG. 12 is a characteristic figure showing the relationship between time and current of the switching element shown in FIG. 11.

The switching element 60 is, as shown in FIG. 11, composed of a transistor 61, resistors 62 and 63, and a capacitor 64.

On the back tip end surface side of the electrode substrate 38A to which the switching element 60 is disposed, a pair of main power supply electrode patterns 38c connected to the through holes 38b, respectively, and the main power supply connecting electrode pattern 38g are disposed.

Each of the main power supply electrode patterns 38c is electrically connected to the electric wire 43 through the through hole 38b. Moreover, the main power supply connection electrode pattern 38g is connected to the main power supply electrode pattern 38c of one side in series by way of the switching element 60.

Therefore, the electric wire 43 of one side is electrically connected to the main power supply connecting electrode pattern 38g, the switching element 60, and the main power supply electrode pattern 38c of one side, and the electric wire 43 of the other side is connected to the main power supply electrode pattern 38c of the other side directly and electrically.

The main power supply electrode pattern 38c and the main power supply connecting electrode pattern 38g mentioned above are closely contacted to the front end surface of the electric conductive rubber 42, and a pair of main power supply electrodes 27C which project from the tip end surface 21a come into contact with the back end surface of the electric conductive rubber 42. The embodiment shown in the drawing is equipped with an electric conductive rubber 42", which is closely contacted to the tip end surface 21a and perforated to form a pair of penetrating holes 42d, through which the main power supply electrodes 27c pass and come into contact with the electric conductive rubber 42.

Because it is constituted in this way, the main power supply electrode 27C of one side comes into contact with the main power supply connecting electrode pattern 38g, thereby being electrically connected to the LED illuminating device 32 through the switching element 60, the main power supply electrode pattern 38c, and the electric wire 43. Moreover, the main power supply electrode 27C of the other side is connected to the LED illuminating device 32 through the main power supply electrode pattern 38c and the electric wire 43.

As a result, because a circuit in which the switching element 60 is installed in an energizing circuit of the power supply is formed, an actual energizing will be started when a predetermined time t1 has passed after the main power supply electrode 27C comes into contact with the electric conductive rubber 42. Therefore, energizing a large current suddenly from the main power supply 10B to the LED substrate 33, or stopping a current suddenly which is energized from the main power supply circuit 10B to the LED substrate 33 does not occur, and hence a rapid current change of the LED illuminating device 32 does not occur.

That is, because a rapid temperature change of the LED illuminating device 32 which is caused by a rapid current change does not occur, the degradation and breakage caused thereby can be controlled and prevented.

It should be noted that although the penetration holes 42d pass through the electric conductive rubber 42" in the above example, it is possible to dispose an electric conductive rubber with no penetration holes 42d, by minimizing the projection height of the main power supply electrode 27C from the tip end surface 21a.

There is concern that the LED illuminating device 32 may be broken by a rapid temperature change (elevation of the temperature). Therefore, in order to prevent such a temperature change, it is preferred to warm the LED illuminating device 32 and maintain the temperature at the time of storage or the like. As an example of such warming and maintain the temperature, it may be exemplified to provide a heating device such as a heater or the like to the adapter case 70 which stores a plurality of kinds of adapters 30, 30A, etc.

Figure 13:
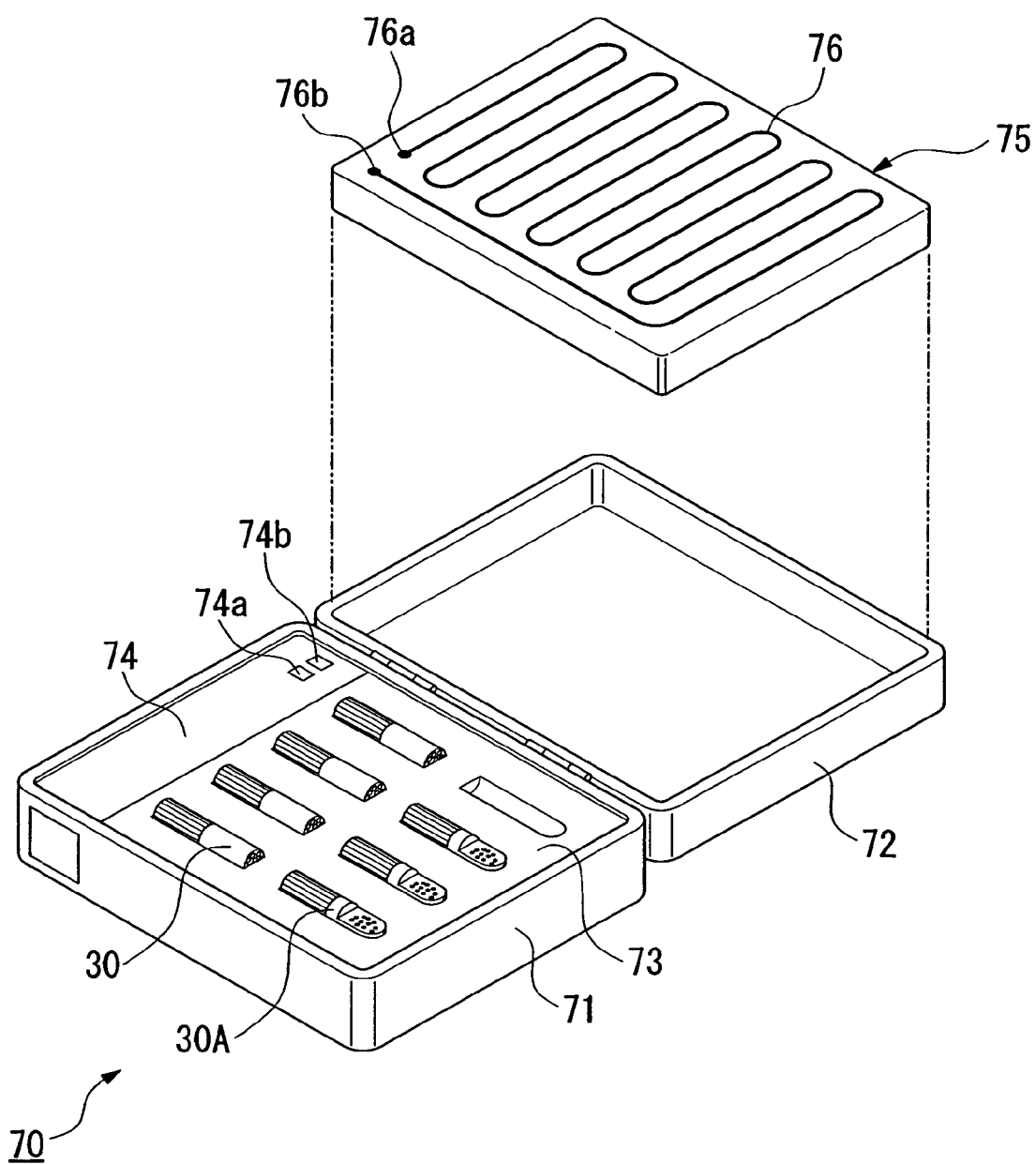
FIG. 13 is a perspective view showing an example of an adapter case equipped with heating and temperature maintenance functions.

In the example shown in FIG. 13, the adapter case 70 is equipped with the main storage body 71 and the opening-and-closing lid 72. The main storage body 71 is composed of the adapter storage part 73 in which a plurality of adapters 30 and the like are stored and a battery 74 which serves as a power supply for the heating device. It should be noted that the battery 74 is equipped with a pair of battery electrodes 74a and 74b which are disposed facing the upper face.

On the other hand, inside the opening-and-closing lid 72, the heater part 75 is disposed as a heating device. The heater part 75 is one in which a heater 76 is substantially uniformly disposed to the front face of the opening-and-closing lid 72. Moreover, the heater electrodes 76a and 76b are disposed in the both ends of the heater 76, such that when the opening-and-closing lid 72 is closed in a predetermined position, the heater electrodes 76a and 76b and the battery electrodes 74a and 74b mentioned above come into contact with each other automatically, thereby performing the heating.

Because the adapter 30 under storage is heated and kept warm at a predetermined temperature by disposing the heating device constituted from such a heater part 75, a rapid temperature change which is caused by being energized when the adapter is started in use can be reduced.

Moreover, as to heating and keeping warm off the adapter 30, it is possible to perform various modifications, in addition to the adapter case 70 mentioned above, such as disposing a heating device such as a heater to a proper place of the storage part 5 shown in FIG. 5A, preferably near the storage position of the adapter 30, thereby warming and maintaining the adapter 30 warm.

It should be noted that the present invention is not limited to the embodiments mentioned above, and can be modified suitably, as long as it does not deviate from the spirit of the present invention; for example, the present invention can be applied to the attachment-and-detachment part of the main body 3 of the endoscope and the insertion part 2, other than the connection of the main power supply circuit in the attachment-and-detachment part which presents between the adapter 30 and the insertion part 2.

Moreover, the present invention makes it possible to energize a usual large current after energizing a relatively small current which passed through a resistance first, by the resistance disposed in the electric circuit to which one electrode either the first electrode or the second electrode mentioned in the above, which comes into contact formerly and loses contact later with the counterpart member, i.e., the electric conductive rubber 42 in attaching-and-detaching operation.

In addition, by the energizing delay device mentioned in the above, it is possible to control the energizing from the main power supply to the LED, thereby preventing a rapid current change.

According to the endoscope apparatus of the present invention mentioned above, the energizing control device for the light emitting diode which operates at the time of attachment-and-detachment operation with the main power supply is disposed in the power supply circuit, and hence a rapid change of the current to be energized to the light emitting diode can be prevented, and as a result, degradation and the breakage of the LED which is caused by a rapid temperature change of the LED are controlled or prevented, thereby improving the life and reliability.

Hereafter, an embodiment of the endoscope apparatus according to the present invention will be explained with reference to drawings.

Fifth Embodiment

First, the fifth embodiment of the present invention will be explained based on FIGS. 14A to 14D, and 18.

Figure 15A:
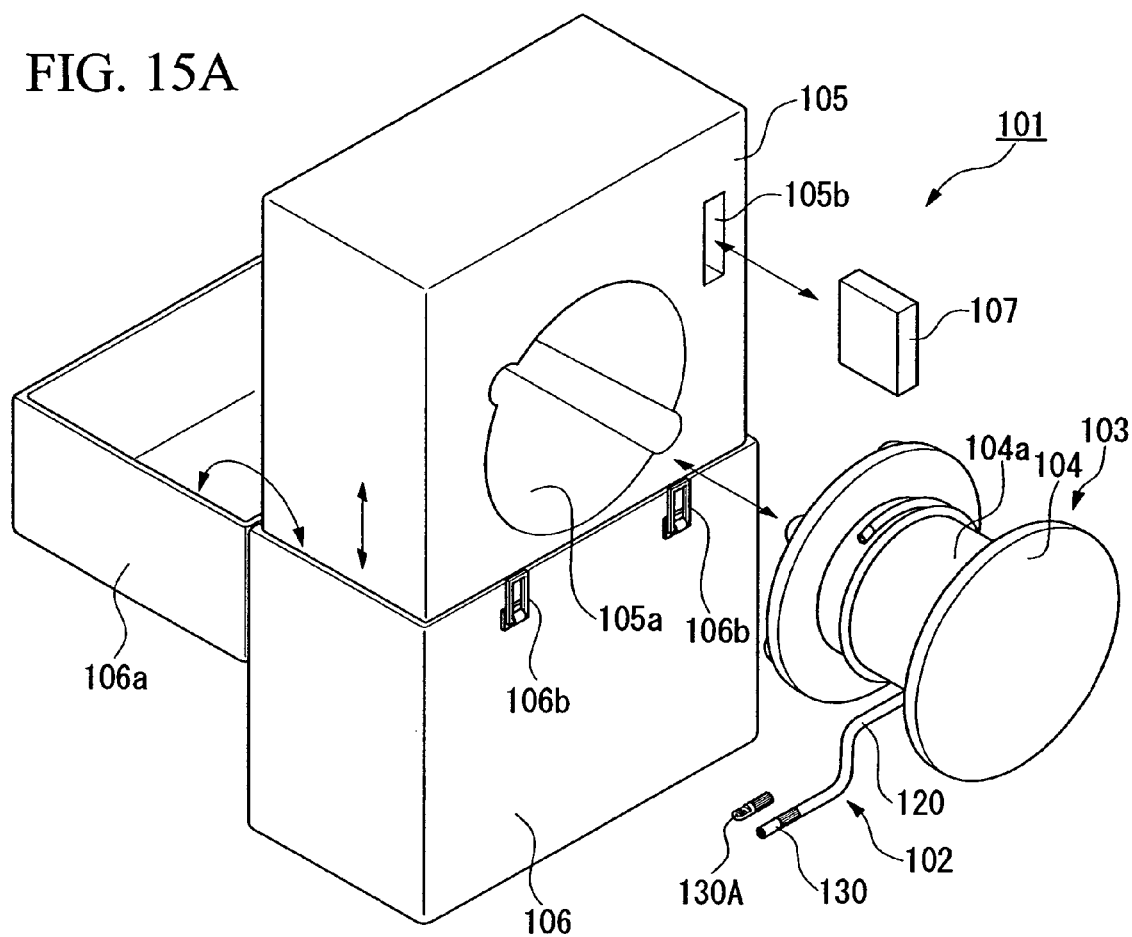
FIGS. 15A and 15B are appearance perspective views showing the entire endoscope apparatus.
Figure 15B:
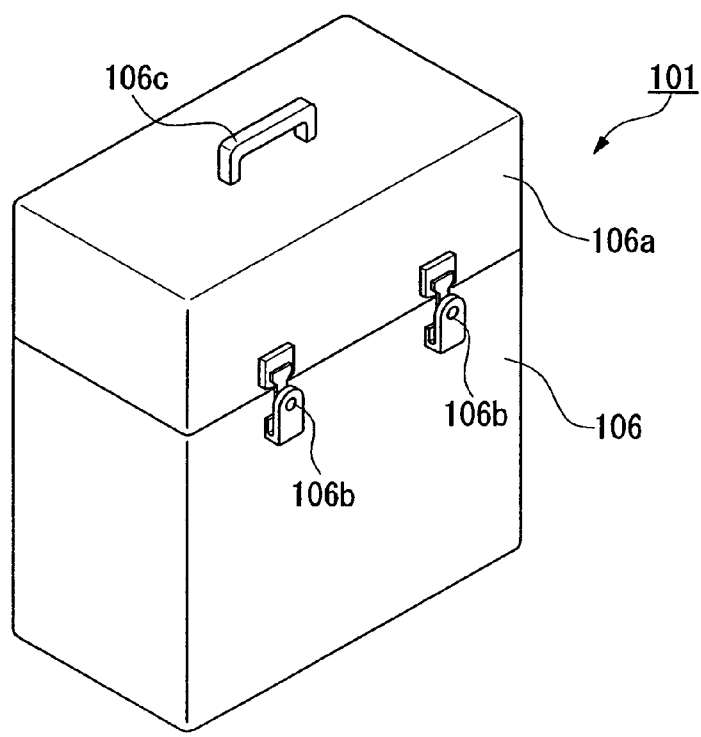

FIGS. 15A and 15B are appearance perspective diagrams showing the whole endoscope apparatus of this embodiment; FIG. 15A shows the state before storing the main body of the endoscope apparatus, and FIG. 15B shows the state where the main body of the endoscope apparatus was stored in the case.

The endoscope apparatus 101 is mainly composed of a main body 103 of an endoscope equipped with a long and fine insertion part 102, and a drum part 104 which reels in and stores the insertion part 102 of the main body 103 of the endoscope apparatus.

The main body 103 of an endoscope is inserted into a recess accommodating portion 105a of an accommodating part 105, in a state where the insertion part 102 is reeled up around the drum part 104, and held there. Thus, the main body 103 of an endoscope as well as the accommodating part 105 is contained in a case 106, and stored and carried in this state. It should be noted that, in the drawings, the reference numeral 105b denotes an accommodate recess of an adapter case 107, the reference numeral 106a denotes an opening-and-closing lid attached to a case 106 by way of a hinge, the reference numeral 106b denotes a tip, and the reference numeral 106c denotes a handle, respectively.

The drum part 104 is, for example, a bobbin form which is composed of an insertion part reeling part 104a having a cylindrical shape on which the insertion part 102 is reeled up (refer to FIGS. 15A), and a pair of disk-like flanges each of which is attached to the upper and lower sides of the insertion part reeling portion 104a.

The drum part 104 is equipped with an image display means, such as an LCD monitor (not shown in the drawings) arranged at proper places (for example, flange etc.). Furthermore, in the inside of the insertion part reeling portion 104a, a battery accommodating part (not shown in the drawings) which accommodates a battery for supplying electrical power, and a cylinder accommodate part (not shown in the drawings) which accommodates a cylinder filled up with a working fluid of a fluid pressure actuator FA mentioned later, and a control part which performs various control are formed. It should be noted that, as the working fluid which is used in a state of being filled in a cylinder, for example, nonflammable gas, such as carbon dioxide, chlorofluorocarbon, nitrogen, helium, argon, and nitrogen, and the like, can be exemplified.

Moreover, a remote controller (not shown in the drawings) which is equipped with a joystick and the like for performing a bending operation of the insertion part 102 mentioned later etc. is connected to the drum part 10fourthrough an operation cable.

Figure 16:
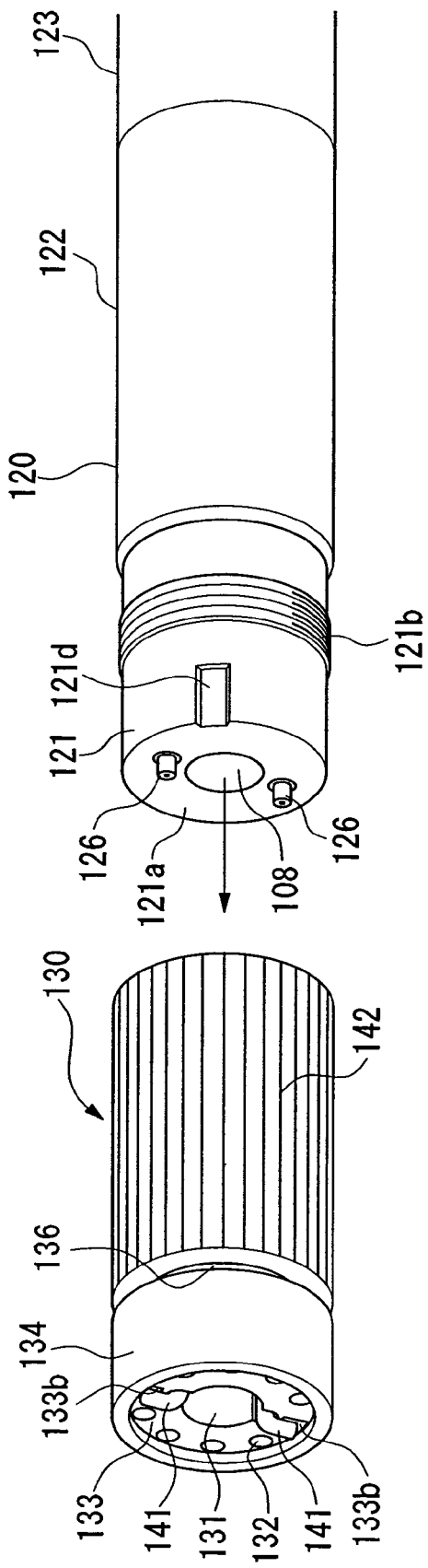
FIG. 16 is a perspective view showing an example of an outline of a tip end part of the insertion part of the endoscope apparatus shown in FIGS. 14A-14D.

As shown in FIG. 16, the insertion part 102 of the main body 103 of an endoscope is constituted from, sequentially from the tip end part inserted into a lumen for observation, an adapter 130 and a flexible tube part 120, each of which is detachably attached to each other.

The adapter 130 is a tip end element which is equipped with an electric apparatus of illumination and the like, and is detachably attached to the tip end of the insertion part 102.

Moreover, a counterpart element to which the adapter 130 is detachably attached serves as a tip end hard part 121 formed on the tip end of the flexible tube part 120. The flexible tube part 120 is composed of the above tip end hard part 121, the bending part 122 for turning the tip end surface of the adapter 130 in the desired observation direction, and a flexible element 123 being flexible and long, which is connected thereto. The bending part 122 is provided on a position slightly behind the tip end hard part 121, and is equipped with two or more of fluid pressure actuators FA for the use of a bending operation, for example, as explained later based on FIG.18.

Moreover, two electrodes (the second electrode) 126 project from the tip end surface 121a of the tip end hard part 121. The electrode 126 is electrically connected to the electric wire which is not shown in the drawings and passing through the inside the insertion part 102, and the electrode 126 is one for supplying electric power to the electric instrument disposed to the adapter 130, from the power supply in the drum part 104 (battery or the like) through this electric wire.

The electrode 126 in this case will be energizable when at least the tip end surface comes into contact with the electrode at the adapter 130 side; for example, the electrode 126 can be energizable by covering the peripheral surface of the electrode 126, which is formed into a columnar shape, such as a cylinder, a prism, a hollow cylinder, or the like.

The adapter 130 is composed of an observation window 131 which is formed, for example at the center of the tip end surface, and a plurality of LED illuminating devices (electric instrument) 132 arranged the observation window 131.

Figure 14A:
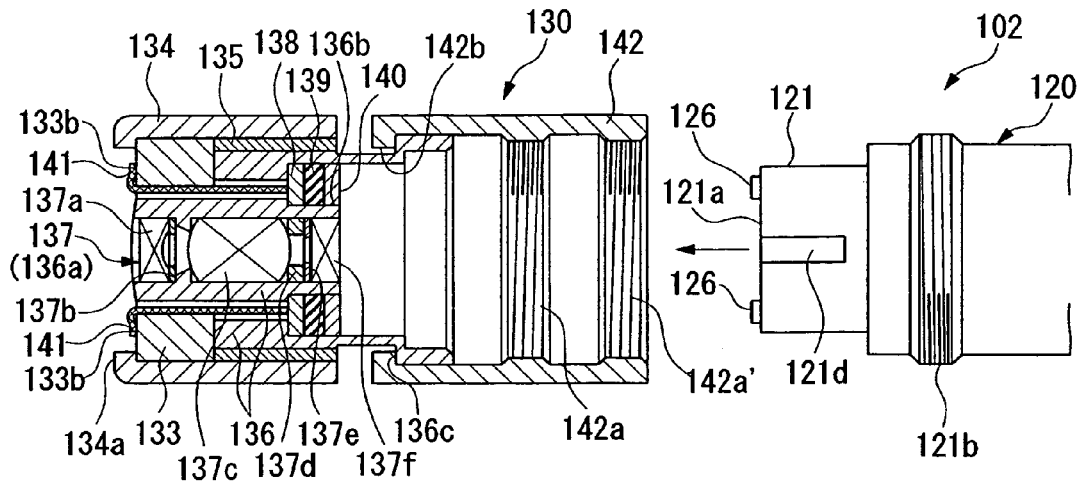
FIGS. 14A-14D show the fifth embodiment of the endoscope apparatus of the present invention.
Figure 14B:
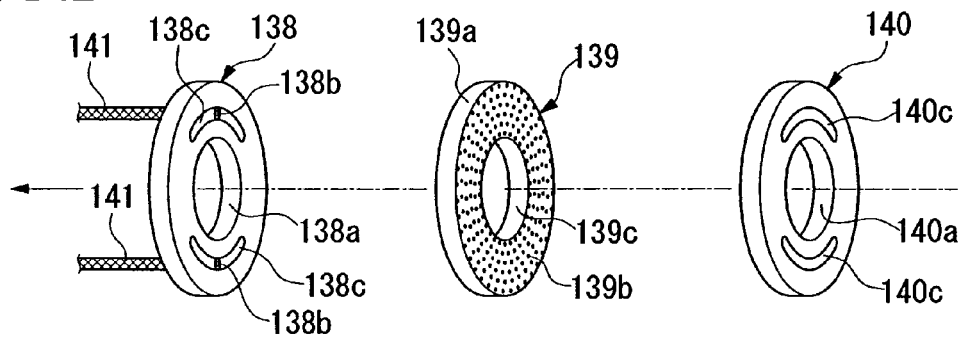
Figure 14C:
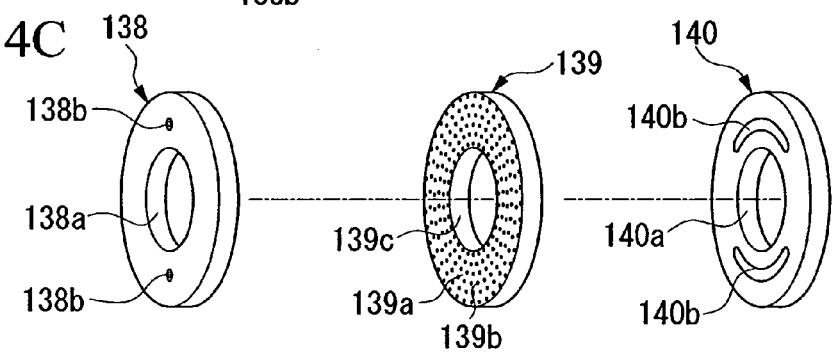
Figure 17A:
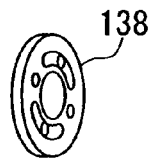
FIGS. 17A-17E are exploded diagram views of the adapter shown in FIGS. 14A-14D.
Figure 17B:
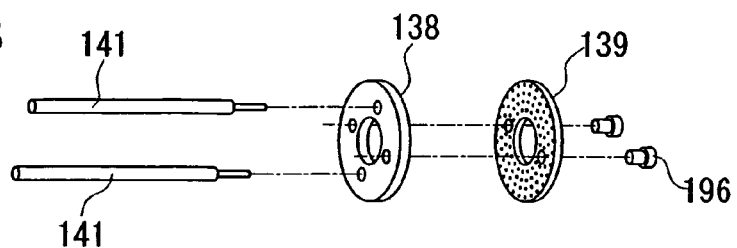
Figure 17C:
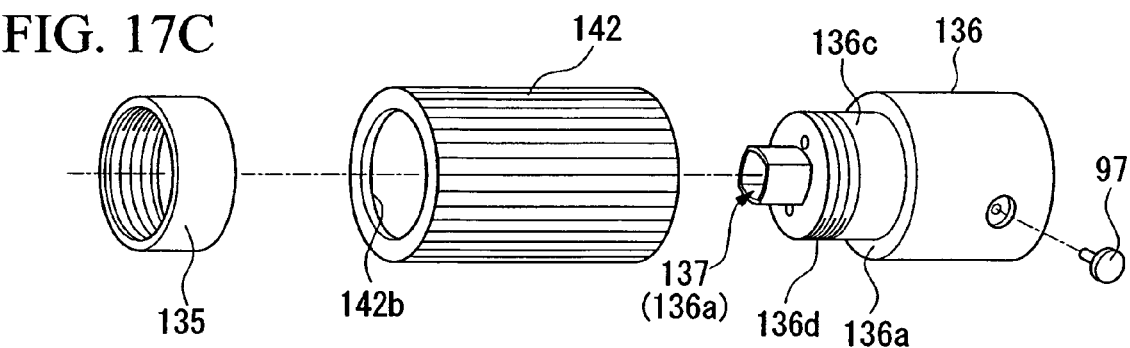
Figure 17D:
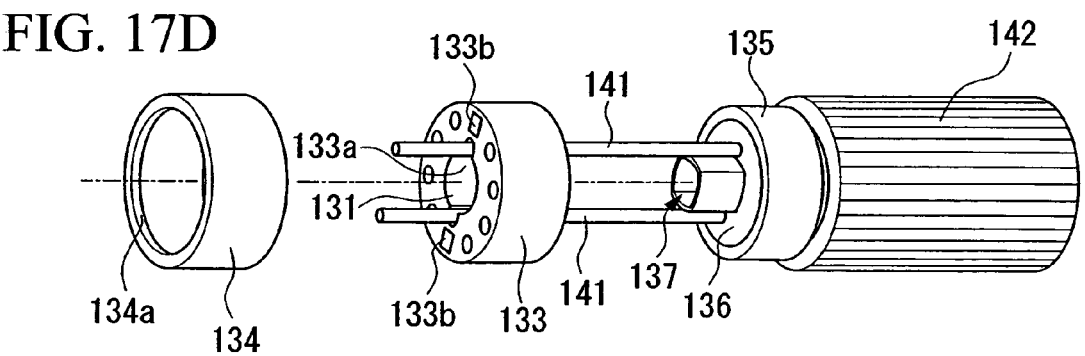
Figure 17E:
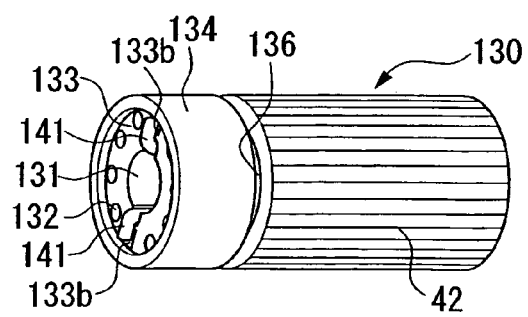

The plurality of LED illuminating devices 132 are arranged in a circumference direction on one surface (front surface) of the LED substrate 133 which is formed into a toroidal shape having a penetrated hole in the center of the disk substrate, The LED substrate 133 is, as shown in FIGS. 14A, 17D and 17E, inserted into a front end of an outer frame member 134 which is formed in approximate a hollow cylinder, and of which locating is performed by abutting the front end surface, on which the plurality of LED illuminating devices 132 are provided, of the LED substrate 133 to a hook part 134a formed by bending the front end of the outer frame member 134 inside.

To the outer frame member 134 into which the LED substrate 133 is inserted, an LED holding part 135 and an LED presser 136 are inserted from an opening formed at a back end side.

An object lens group 137 which serves as an optical lens system is provided to a space part 136a formed along the axial center of the LED presser 136. In an example shown in the drawings, the object lens group 137 is constituted from the first lens 137a, a spacer 137b, the second lens 137c, a spacer 137d, an iris diaphragm 137e, and the third lens 137f, each of which is arranged in this order sequentially from the tip end surface, on which an opening is formed, along the direction of an axis.

The first electrode substrate 138, an elastic member (it is hereafter referred as "electric conductive rubber") 139 having different direction conductivity, and the second substrate 140 are inserted sequentially from the tip end surface side at the perimeter side, into an inner cylinder part 136a of the LED presser 136 which forms the space part 136a. The electrode substrate 138 has a toroidal shape which is formed by penetrating a penetrated hole 138a at the center of a disk shaped resin substrate (referred as a "disk" hereinafter), thereby making positioning easy, and two through holes 138b are formed outside of the penetrating hole 138a, each of the pair of through holes 138b is formed on upper and lower sides of the resin substrate with respect to the penetrated hole 138a, and the inner surface of each of the pair of through holes 138*b* is coated with a conductive material. To these through holes 138*b*, electric wires 141 for supplying electric power for the LED illuminating 132 to the LED substrate 133 are electrically connected respectively, by soldering and the like.

Moreover, on the back end surface of the first electrode substrate 138, a pair of electrode patterns (the first electrode) 138*c* consisting of an upper one and a lower one, are provided independently, respectively. These electrode patterns 138*c* are electrically connected to a conductive material which covers the inner surface of the through hole 138*b*, respectively.

The electrode pattern 138*c* is independent from every pair of through holes 138*b*, in other words, each of the pair of the electrode patterns 138*c* is isolated from the others, so that short-circuit is avoided, and each of them is formed to be a circular arc shape.

The circular electrode pattern 138*c* mentioned above can be omitted, and it is possible to provide simply an electrode composed of a conductive member which is exposed to the both ends of the through hole 138*b*.

In addition, the other end of the electric wire 141 mentioned in the above passes along the electric wire passage formed between the LED board 133 and the LED presser 136, and is connected to the electrode part 133*a* provided on the tip end surface of the LED substrate 133.

An electric conductive rubber 139 is composed of many conductive members 139*b* arranged in dots on the elastic body 139*a* being an insulator, and the electric conductive rubber 139 is, for example, an anisotropic rubber.

The electric conductive rubber 139 is one constituted from the elastic body 139*a* which is made of a silicone rubber sheet or the like, and conductive members 139*b* such as metal particles or nickel particles on which gold plating is deposited, or the like, arranged in a thickness direction of the elastic body 139*a*.

Therefore, by pressing the electric conductive rubber 139 lightly in the thickness direction thereof, the electrical conductivity between the conductive members 139*b* of which density is increased, and a good electrical connection in the thickness direction thereof can be attained. However, because the elastic body 139*a* is an insulating member, the conductive rubber 139 has insulation properties except in the thickness direction thereof (for example, the direction of a circumference). In this case, each of the conductive members 139*b* arranged in dots (the portions exposed to both surfaces have dot shape) is isolated by insulating member from each other, thereby forming a non-conductive and independent state.

Moreover, similar to the above first substrate 138, the conductive rubber 139 is formed into a toroidal shape with a penetration hole 139*c* at the center thereof, thereby making positioning easy.

The second substrate 140 is formed into a toroidal shape where the penetration hole 140*a* was perforated at the central part of a disk, and a pair of electrode patterns 140*b* and 140*c* which are formed into a circular shape respectively are disposed outside the penetration hole 140*a* on both sides thereof, i.e., the front end surface and the back end surface. In this case, the electrode pattern 140*b* of the front end surface and the electrode pattern 140*c* of the back end surface are electrically connected to each other by a circuit pattern, a through hole, or the like, formed in the substrate. In addition, as for the electrode patterns 140*b* and 140*c* in this case, each of which circular parts is isolated from each other, so that it may not be connected to form a short circuit.

Figure 14D:
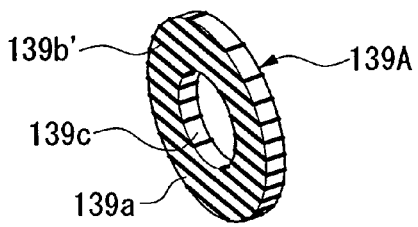

Although the electric conductive rubber 139 of the dot type having a plurality of electric conductive members 139*b* arranged in the shape of a dot was adopted in the above embodiment, it is also possible to use a stripe type electric conductive rubber 139A as shown, for example, in FIG. 14D. Stripe type electric conductive rubber 139A is constituted from an elastic body 139*a* which is an insulator formed into a disk shape, and a plurality of electric conductive members 139*b*' each of which is disposed in a thickness direction of the electric conductive rubber 139A so as to be in a stripe form on the elastic body 139*a*. In this case, each of the electric conducive members 139*b*' which are arranged in a stripe form (the portions exposed to both surfaces and each of cross sections are formed into a stripe shape) is isolated from each other by an insulator to be in an independent state.

It should be noted that as for the stripe-like conductive members 139*b*', the arrangement direction and the arrangement shape (for example, a parallel arrangement) thereof is not particularly limited, as long as each of them is isolated from each other.

A connecting ring 142 is disposed rotatably at the perimeter back end side of an LED presser 136. The connecting ring 142 is substantially a cylindrical member having an inner thread part 142*a* on the inner surface, which engages with an outer thread part 121*b* formed on the perimeter of an insertion part 102 mentioned later.

The LED presser 136 penetrates the connecting ring 142, and a step part 136*c* of the LED presser 136 engages with an engage part 142*b* formed on the tip end of the connecting ring 142 to prevent the connecting ring 142 from dropping out in an axial direction of the connecting ring 142.

It should be noted that an inner thread part 142*a*', which prevents the connecting ring 142 from dropping out of the insertion part 102, is formed on the back end side of the inner surface of the connecting ring 142.

Here, the assembling method of the adapter 130 will be explained referring to FIGS. 17A to 17E. First, a pair of electric wires 141 are connected to the first substrate 138, respectively, and the electric conductive rubber 139 is fixed to the first substrate 138 by a pair of fixing pins 196 to form a unit. It should be noted that, as the unit, one having a sandwich constitution may be usable, which is composed of the first electrode 138, the second electrode 140, and the electric conductive rubber 139 sandwiched therebetween.

Next, the positioning pin 197 is inserted in the LED presser 136, and is fixed by an adhesive or the like, and then the connecting ring 142 is connected to the LED presser 136. Here, the locking part 142*b* of the connecting ring 142 can be connected to an outer thread part 136*d* of the LED presser 136 by way of a screw and nut relationship formed therebetween, and hence, in the case of screwing it in to the end, the locking part 142*b* reaches the position of the step 136*c* to be fixed there.

Thereafter, the LED holding part 135 is connected to the outer thread part 136*d* of the LED presser 136. In this state, the unit consisting of the first substrate 138, the electric conductive rubber 139, and the electric wires 141 are inserted through the opening of the connecting ring 142 and then the tip ends of the electric wires 141 are dragged out, respectively.

Then the LED illuminating device 133 is inserted in the tip of the LED presser 136 from the tip end side, and the electric wires 141 are cut to suitable length, respectively, and are connected to the electric wires 133*b* of the LED illuminating device 133, respectively, by soldering or the like. Finally, an outer frame member 134 is fixed to the LED holding part 135 by screws (which are not shown in the drawings).

Thus, the second electrode substrate 140 which supplies electric power to the LED illuminating device 132 is exposed to the inside of the adapter 130 having the LED illuminating device 132 at the tip end surface thereof, through the opening at the back end side of the connecting ring 142 and the LED presser 136. In other words, the second electrode substrate 140 is disposed such that the second electrode substrate 140 is exposed to the inner surface of the adapter 130 which faces to a tip end surface 121a of the insertion part 102 in the connected state.

It should be noted that such an adapter 130 includes, for example, as shown in FIG. 14A, an adapter 130A for side viewing which is equipped with an observation window or an LED illuminating device on the side (circumference side) and an adapter of which object lens group 137 constitution and optical specification differ, in addition to the above one for a direct-vision which is equipped with the observation window 131 and the LED illuminating device 132 on the tip end surface.

In the tip end hard part 121 of the insertion part 102, in order to pick up the image captured from the observation window 31 of the adapter 30 through the object lens group 137, for example, a CCD 108 is installed as an observation device. The CCD 108 is connected to the main body 103 of the endoscope through a cable 108a passing through the inner space of the insertion part 102, and the CCD 108 transmits image signals picked up while receiving electrical power supplied from the inside of the drum part 104. It should be noted that the above observation device is not limited to CCD 108, and may be a C-MOS, an image guide fiber, or the like.

Figure 18:
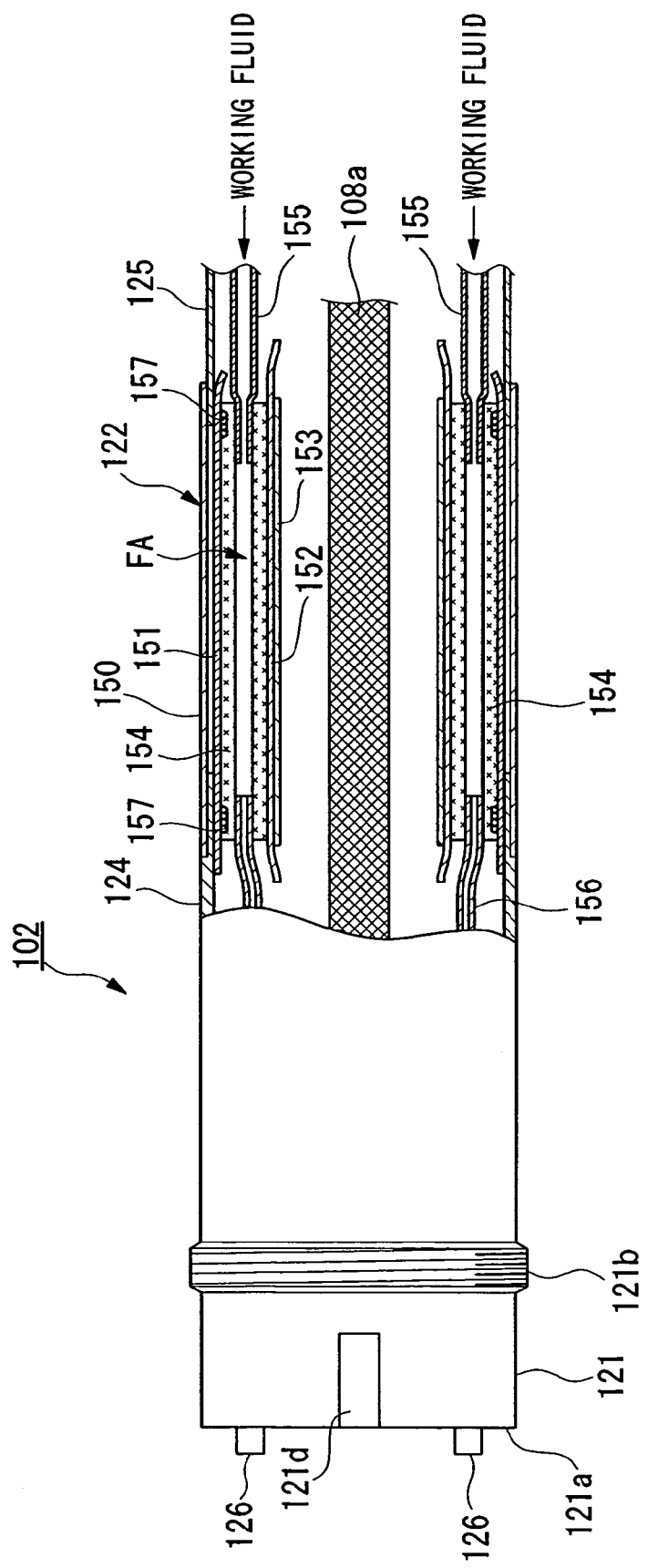
FIG. 18 is a principal part sectional view showing an example using a fluid actuator at the bent side on the tip end of an insertion part.

A fluid actuator FA is disposed between the front cap 124 connected to the tip end hard part 121 and the back cap 125 connected to the flexible member 123, as shown in FIG. 18.

The fluid actuator FA is constituted from an outer coil pipe 150, an outer tube 151, an inner tube 152, an inner coil pipe 153, and a multi-lumen tube 154 the outer coil pipe 150 and the outer tube 151 are connected to the front cap 124 and the back cap 125, respectively, such that each of the front cap 124 and the back cap 125 is interposed between the outer coil pipe 150 and the outer tube 151 at both ends of the outer coil pipe 150 and the outer tube 151.

The inner tube 152 and the inner coil pipe 153 are inserted inside the outer coil pipe 150 and the outer tube 151, and the multi-lumen tube 154 is disposed between the inner tube 152 and the outer tube 151.

The multi-lumen tube 154 is a member having a substantially circular cross-section, which is made of a flexible silicone material, and is equipped with a plurality of (for example, at four places at a 90-degree pitch) air chambers each of which is formed at an equivalent pitch in a direction of the circumference.

As for the multi-lumen tube 154, one end of the air chamber is connected to a working fluid feed pipe 155, and the other end is connected to the connection tube 156. The working fluid feed pipe 155 at one side is connected to the cylinder of the main body 103 of the endoscope so as to supply the working fluid to the air chamber of the multi-lumen tube 154. It should be noted that the other end of the connection tube 156 is connected to a pressure sensing means (which is not shown in the drawings) which detects, for example, the pressure of the working fluid to perform feedback control.

The outer coil pipe 150 and the inner coil pipe 153 in the above are tubular members (a closely contacted coil) which are, for example, made of stainless steel which bends easily. Moreover, the outer tube 151 and the inner tube 152 are thin tubes which are, for example, made of fluoride, and which prevent the multi-lumen tube 154 from being inserted between the lines of the outer coil pipe 50 and the inner coil pipe 53, thereby being broken. It should be noted that the reference numeral 157 in the drawings denotes a wound yarn for fixation.

Because the fluid actuator FA constituted in the above bends at a stretched side where the multi-lumen tube 154 is expanded by the supplied working fluid, what is necessary for bending the fluid actuator FA is substantially to supply the working fluid to the multi-lumen tube 154 at an opposite side of the direction (the direction of 180 degrees) in which it is desired to curve, thereby making it expand.

In addition, of course the means for bending the bending part 122 is not limited to the above fluid actuator FA, for example, other well-known device, such as a wire type, or the like can be used.

In the endoscope apparatus 101 with such a constitution, after selecting a desired adapter 130 and inserting the tip end of the insertion part 102 into the back end side opening of the connecting ring 142, the connecting ring 142 is rotated to be connected to the insertion part 102.

In this time, at first, the thread part 121b engages with the inner thread part 142a' of the connection ring 142 outside the tip end hard part 121, and if the rotating of the connection ring 142 is continued further, the outer thread part 121b transits the inner thread part 142a' to progress to the tip end side, thereby being released from being engaged with the inner thread part 142a'. As a result, the outer thread part 121b reaches a space between a pair of the inner thread parts 142a and 142a' having a predetermined interval to be free, and hence the inner thread part 142a' abuts on the outer thread part 121b, thereby functioning as a stop which prevents the adapter 130 from dropping out of the flexible tube part 120.

In the case of rotating the connecting ring 142 further, with squeezing the insertion part 102 therein, from such a space where the dropping out is prevented, at this time the outer thread part 121b is screwed with the inner thread part 142a, and hence the adapter 130 is connected to the insertion part 102 in a state where the adapter is fixed to a predetermined position with respect to the tip end of the insertion part 102.

It should be noted that the reference numeral 121 d in the figure denotes a concave groove part which is formed for positioning in a direction of circumference, which performs the positioning by engaging with a convex part, which is not shown in the drawing, and is formed on an inner circumference surface of the LED presser 136.

In the case in which the adapter 130 is connected to the insertion part 102 in the predetermined position mentioned above, the main electrode 126 which projects from the tip end surface 121a at first abuts on the electrode pattern 140c of the second substrate 140, thereby pressing the second substrate 140 in the direction of the tip end part. Therefore, the electric conductive rubber 139, which is made of an elastic body and interposed by the first electrode substrate 138 of which movement to the tip end part side is prevented by the LED presser 136, is compressed, such that the density of the electrical conductive members 139b which are arranged in a thickness direction of the electrical conductive rubber 139 is increased, thereby improving the electrical conductivity to form a energizing state.

In addition, because the electric conduction rubber 139 interposed between the first substrate 138 and the second substrate 140 is an elastic body, and close contact is formed between the electrode pattern 138b of the first substrate 138 and the electric conductive rubber 139, and between the electrode pattern 140b of the second substrate 140 and the electric conductive rubber 139, it is possible to energize reliably from the electrode 126 to the electric wire 141 by way of the electric conductive rubber 39 of which electric conductivity has been improved.

Because such an electrical conductive state is formed as only one direction of the thickness direction due to the characteristic of the electric conductive rubber 139, the direction of the circumference will not be in an electrical conductive state, for example. Therefore, because it is not necessary to arrange an insulating member around the electric conductive rubber 139, space reservation for an insulating member becomes unnecessary and hence the structure of the electrode can be miniaturized.

In the embodiment mentioned above, the concave storage portion 105a is formed in the side of the storage part 105, and the main body 103 of the endoscope is stored, and the main body 103 of the endoscope as well as the storage part 105 are taken in and out of the inside of the case 106, it is possible to form a concave storage position or the like in the upper surface of the storage part. Moreover, it is possible that the storage part which consists of cushion material or the like is formed in the case 106, such that the main body 103 of the endoscope apparatus is taken in and out from an upper position through an opening which is perforated at the upper surface of the concave storage portion.

Figure 19A:
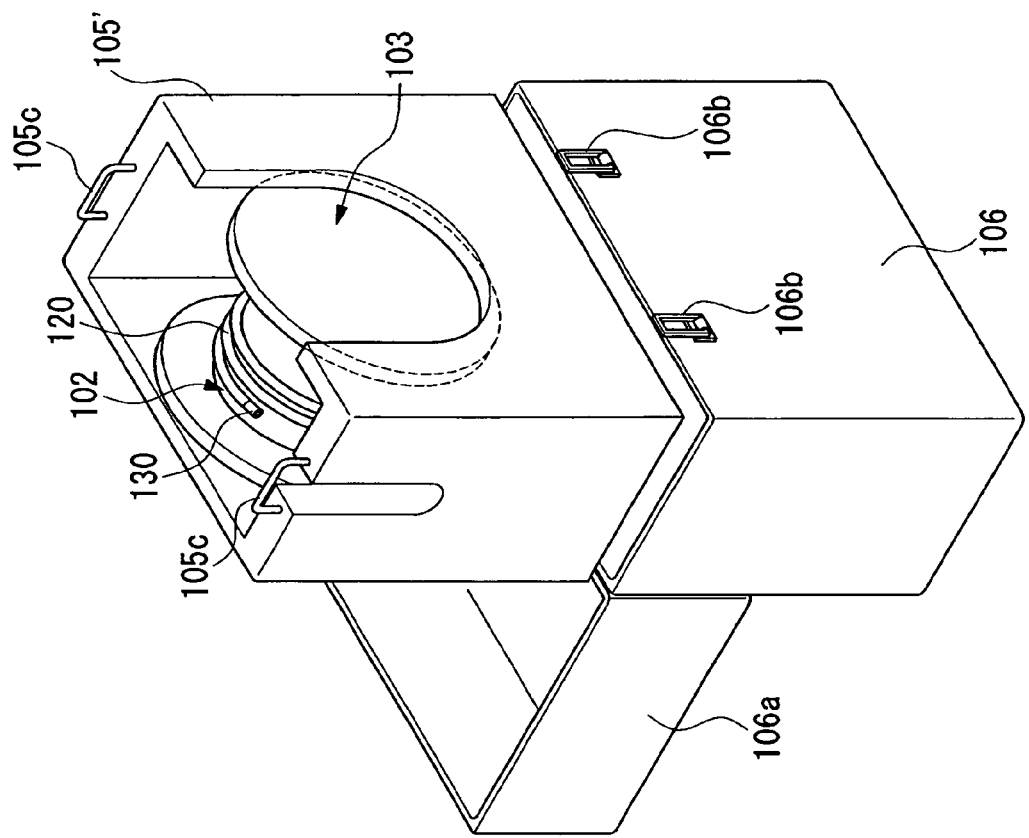
FIGS. 19A and 19B are appearance perspective views showing the first modification of the entire endoscope apparatus.
Figure 19B:
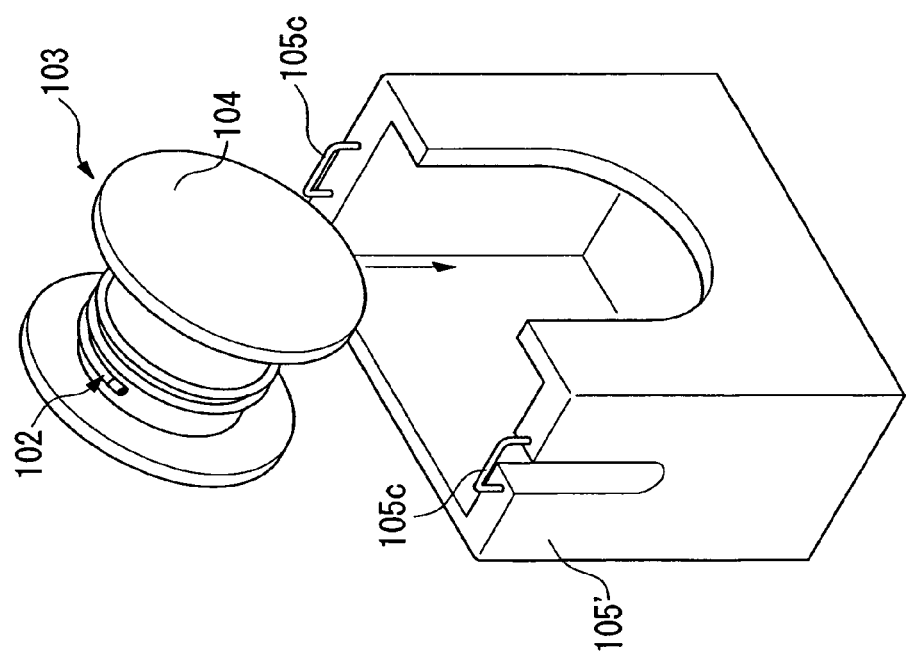

Furthermore, as the first modification shown in FIGS. 19A and 19B, it is also possible to constitute it, such that the upper face and one side face are opened and the main body 103 of the endoscope apparatus is stored in the storage part 105' to which a pair of handles 105c are disposed, and that the main body 103 of the endoscope apparatus as well as the storage part 105' are taken in and out from the case 106 through the upper face of the case 106 of which open-and-disclose lid 106a is opened.

Figure 20A:
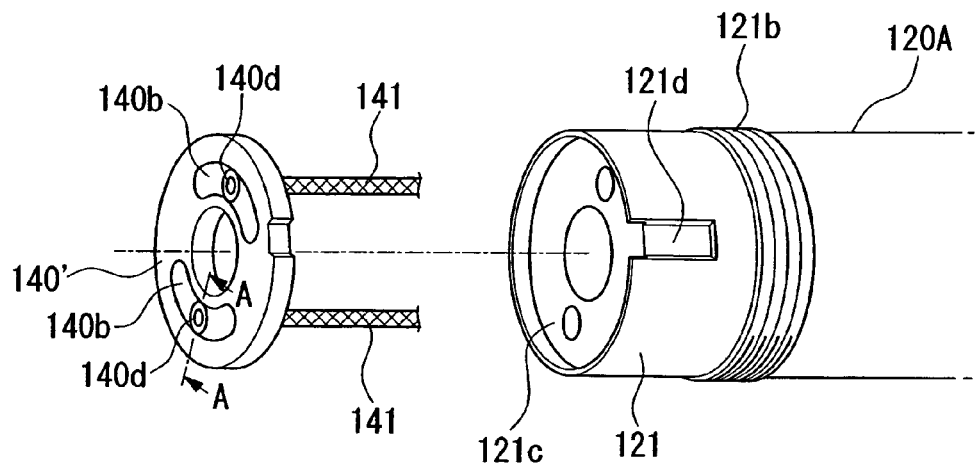
FIGS. 20A and 20B are exploded perspective views of the principal part showing the second modification of the endoscope apparatus of the first embodiment of the present invention.
Figure 20B:
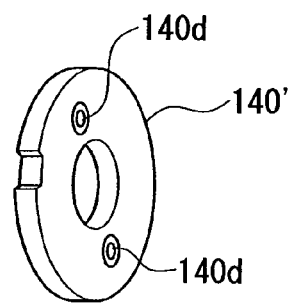
Figure 21:
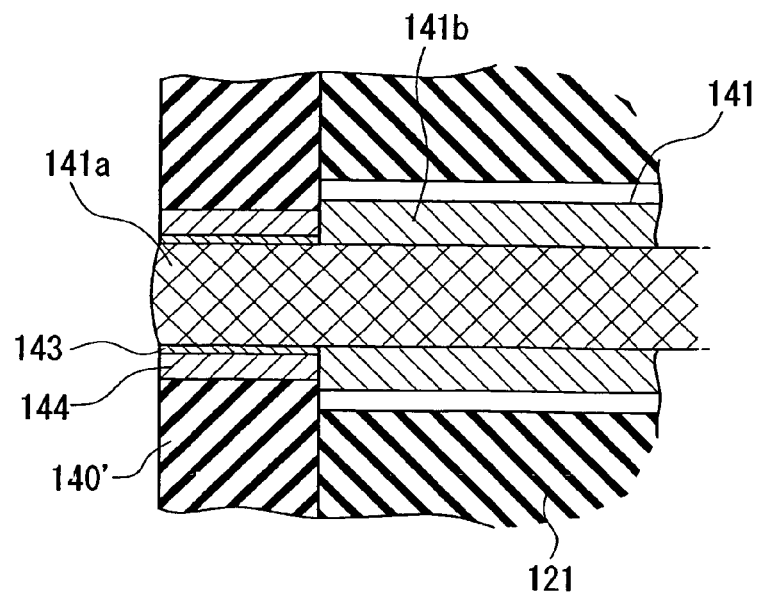
FIG. 21 is a sectional view taken along line A-A in FIG. 20A.

Moreover, although in the above embodiment, the second substrate 140 was disposed to the adapter 130 side, the second substrate 140 can be disposed to the flexible tube 120 side, as the second modification shown in FIGS. 20A and 21.

In the second modification, the second substrate 140' in which a pair of through holes 140d are disposed is used. The second substrate 140' is attached to a concave portion 121c which is formed at the tip end surface of the flexible tube 120. That is, as a substitute for the electrode 126 in the fifth embodiment mentioned above, an electric conductive member 141a of the electric wire 141 is made to project from the tip end surface of the second substrate 140', such that the projected portion serves as an electrode. The electric conductive member 141a penetrates the through hole 141d, and is electrically connected to the conductive layer of the through hole 141d through the solder 143 and is fixed.

Moreover, the electric conductive layer 144 of the through hole 141d is electrically connected to the electrode pattern 140b. It should be noted that the reference numeral 141b in the drawings denotes the covering layer of the electric wire 141.

On the other hand, because the first substrate 138 and the electric conductive rubber 139 remain in the adapter 130 side in this order from the tip end side, by inserting and connecting the insertion part 102 to the predetermined position of the adapter 130, the electric conductive rubber 139 will be interposed between the first substrate 138 and the second substrate 140' to be compressed therebetween. For this reason, because close contact to the electrode will be formed, similarly to the first embodiment mentioned above, while the conductivity of the electric conductive rubber 139 increases, and hence it is possible to energize reliably from the electric conductive part 141a at the second substrate side to the electric wire 141 at the first substrate 138 side by way of the electric conductive rubber 139f.

Figure 22:
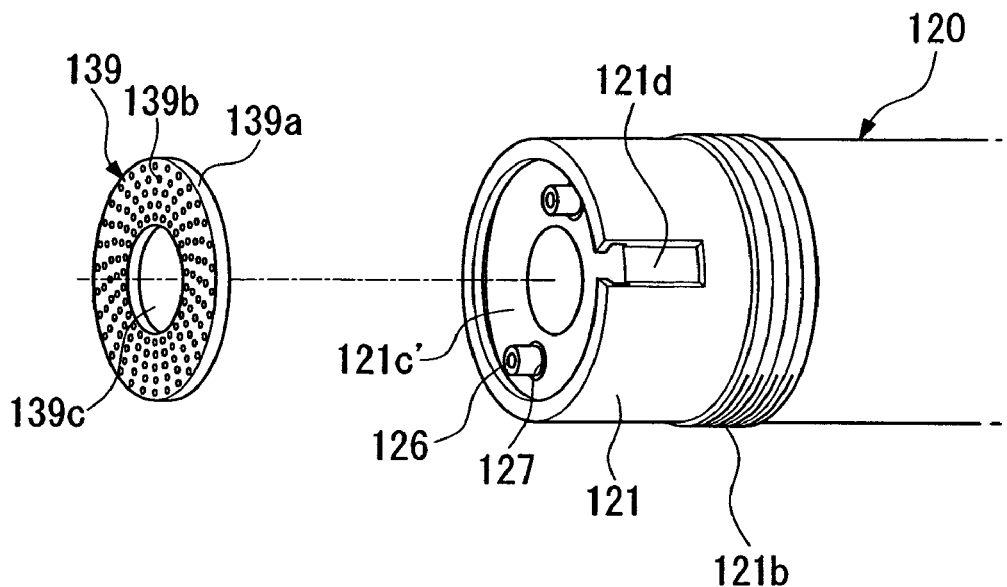
FIG. 22 is a perspective view showing the third modification of the endoscope apparatus of the first embodiment of the present invention.

Moreover, as the third modification shown in FIG. 22, the electric conductive rubber 139 may be disposed to the concave portion 121c' which is formed on the tip end surface of the flexible tube part 120, thus the electric conductive rubber 139' can be interposed so as to be compressed in this form. Therefore, because a close contact to the electrode 126 can be obtained while the conductivity of the electric conductive rubber 139 increases, it is possible to energize reliably by way of the electric conductive rubber 139 in a predetermined connection state. It should be noted that the reference numeral 127 in the FIGure denotes the insulator disposed between the electrode 126 and the tip end hard part 121.

Figure 23:
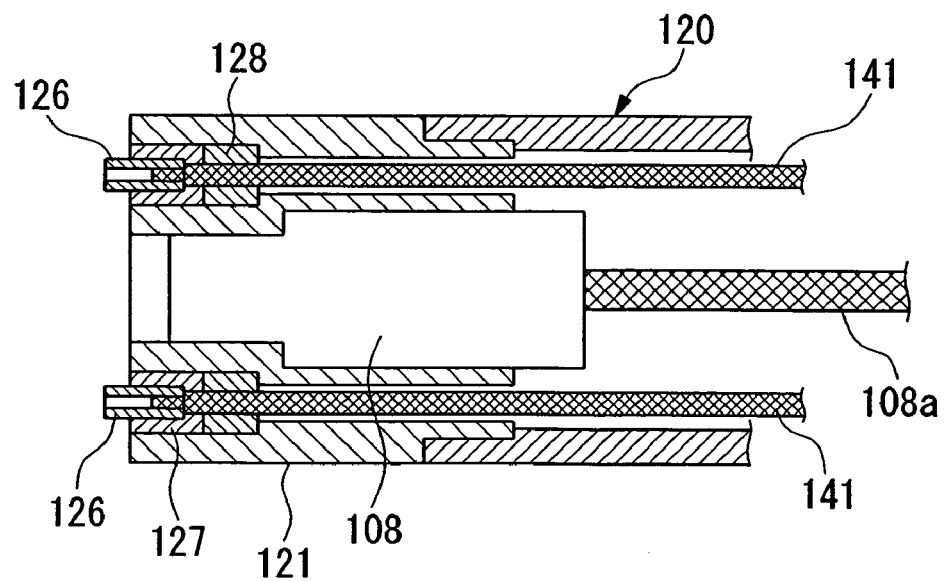
FIG. 23 is a principal part sectional view showing the fourth modification of the endoscope apparatus of the first embodiment of the present invention.
Figure 24A:
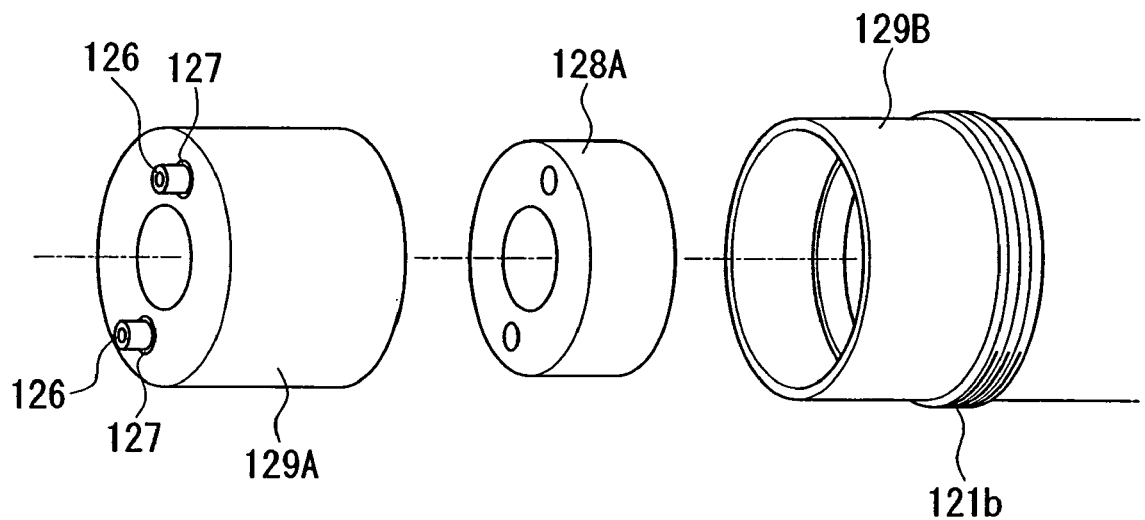
FIGS. 24A and 24B are figures showing the fifth modification of the endoscope apparatus of the fifth embodiment of the present invention.
Figure 24B:
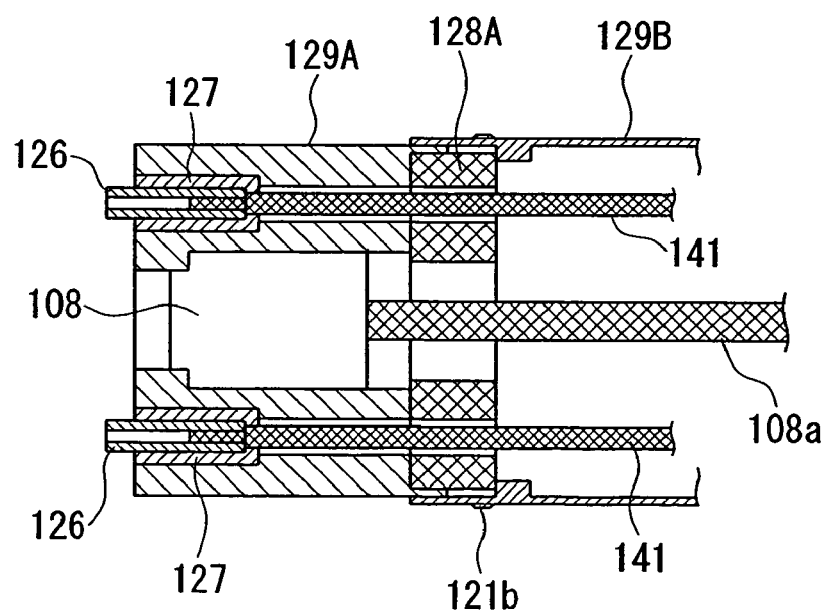

In addition, in the fourth and the fifth modifications shown in FIGS. 23, 24A and 24B, in order to compensate the elasticity of the electric conductive rubber 139, the elastic body 128 as a separate body is disposed at appropriate locations.

In the fourth modification shown in FIG. 23, the elastic body 128 is disposed behind the electrode 126 which projects from the tip end surface 121a of the flexible tube part 120, thereby compressing the elastic body 128 in the predetermined connection state.

By constituting in this way, the elasticity present in the elastic body 128 can be add to the elasticity present in the electric conductive rubber 139, thereby making the contact be closer. In other words, it is possible to make the electric conductive rubber 139 be thinner, and to compensate for the elasticity by the elastic body 128. It should be noted that the thinner the thickness of the electric conductive rubber 139, the easier the production of the electric conductive rubber 139.

Moreover, in the fifth modification shown in FIGS. 24A and 24B, an elastic body 128A is disposed between a tip end member 129A which is a separate body being movable in an axial direction and a tip end receptor 129B. Even in such a constitution, the elasticity present in the elastic body 128A can be added to the elasticity of the electric conductive rubber 139, and hence it is possible to make the contact be closer.

Sixth Embodiment

Next, the sixth embodiment of the endoscope apparatus of the present invention will be explained based on FIGS. 25A, 25B, 26A, and 26B. It should be noted that the same reference numerals are given to the corresponding portions as in the above embodiments, and the detailed explanation thereof is omitted.

Here, although in the fifth embodiment mentioned above, the case where the present invention was applied to the adapter 130 for a direct-vision, in the following embodiments, applications of the present invention to the adapter 130A for side viewing are shown and explained.

Figure 25A:
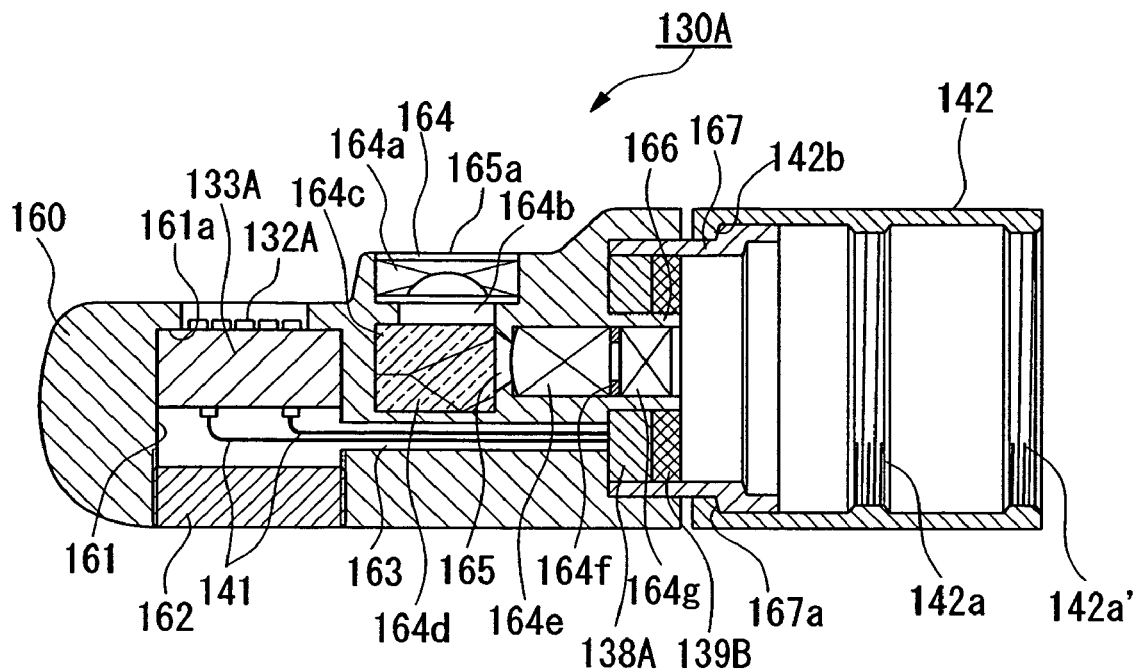
FIGS. 25A and 25B are figures showing the sixth embodiment of the endoscope apparatus of the present invention.
Figure 25B:
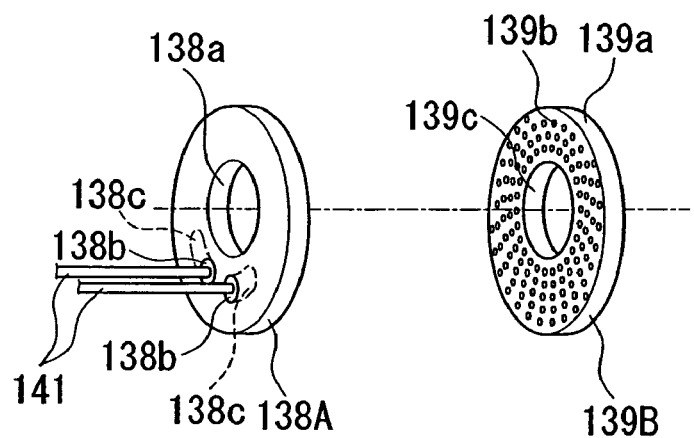
Figure 26A:
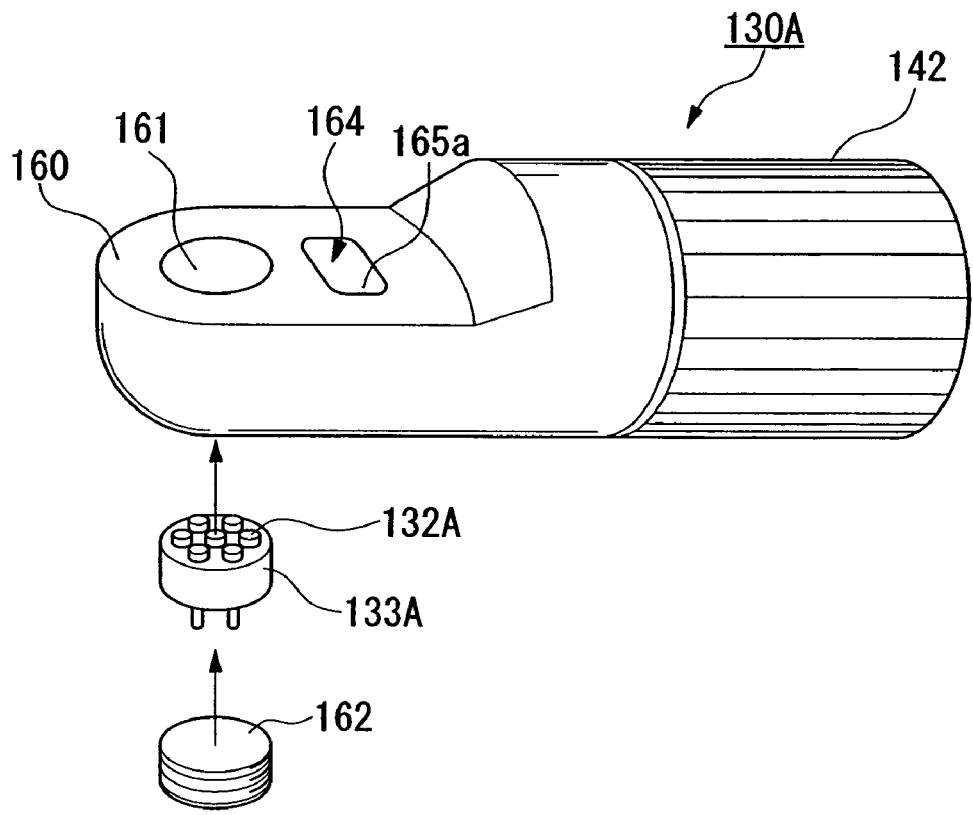
FIGS. 26A and 26B are figures showing the adapter for side viewing shown in FIGS. 25A and 25B.
Figure 26B:
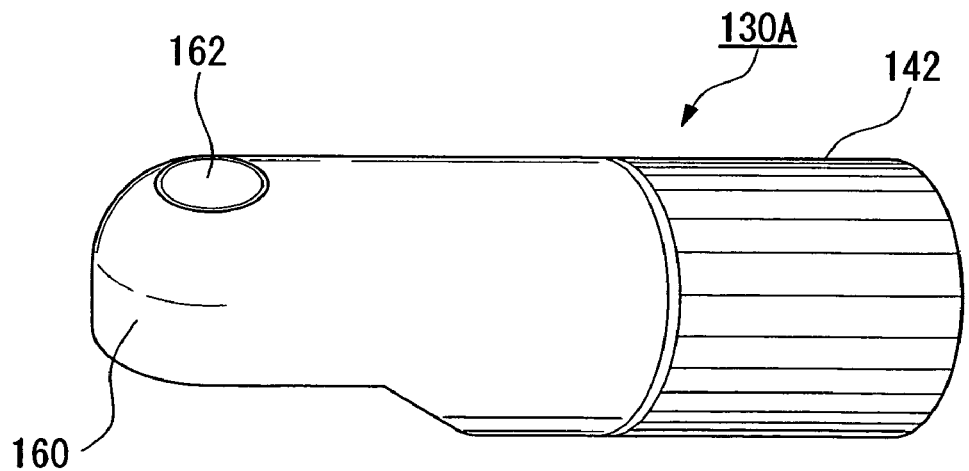

The adapter 130A for side viewing shown in FIGS. 25A, 26A, and 26B is a integrated body which is constituted from the tip end frame member 160, the intermediate ring member 167 which has a stepping part 167a for engaging the connecting ring 142, and the connecting ring 142 mentioned above.

The penetration hole 161 having an approximately cylindrical shape which intersects perpendicularly with the axial direction and is formed at a proper place near the tip end part of the tip end frame member 160. The stepping part 161a is formed in the penetration hole 161, into which the LED substrate 133A is inserted from one entrance opening, such that the LED illuminating device 132A turns to an outside (side). The LED substrate 133A is positioned by abutting a perimeter portion of the LED substrate 133A on the stepping part 161a, and is fixed by a suitable means thereafter. In this way, after fixing the LED substrate 133A to a predetermined position, the sealing member 162 is screwed to an entrance opening to be closed.

Moreover, inside the tip end frame member 160, the electric wire passage 163 is formed in the axial direction which intersects perpendicularly with the penetration hole 161. The electric wire passage 163 is a passage (space) through which the electric wire 141 for supplying electric power supplied from the main body 103 to the LED substrate 133A passes. One end of the electric wire 141 is connected to the LED substrate 133A and the other end of the electric wire 141 is connected to the first substrate 138A mentioned later.

Furthermore, to the tip end frame member 160, a space part 165 for installing the object lens group 164 is formed to be curved in approximately the shape of an L, such that the opening in a side direction which is formed to intersect perpendicularly with the axial direction forms an observation window.

It should be noted that the illustrated object lens group 164 is constituted from the first lens 164a, the spacer 164b, the second lens 164c, the third lens 164d, the fourth lens 164e, the iris diaphragms 164f, and the fifth lens 164g sequentially from the side opening (observation window) side of the tip end frame member 160.

In the inner side of the tip end frame member 160, the first substrate 138A and the electric conductive rubber 139B are inserted, sequentially from the tip part side, in the perimeter of the inner cylinder part 166 which is an extension of the space part 165 in the axial direction, which stores the object lens group 164. Although the first substrate 138A and the electric conductive rubber 139B in this case form substantially the same constitution as the fifth embodiment mentioned above, it differs in that the position of the penetration holes 138a and 139a is decentered. This is because the LED illuminating device 132A and an observation window are disposed to the side of the tip end frame member 160 of which diameter becomes thin, this originates in the direction arrangement of an axis of the optical lens group 164 or the electric wire 141 shifting from an axial center, and therefore it may be disposed to the center depending on situations, such as space reservation.

In such a constitution, when the insertion part 102a is inserted to a predetermined position and connected, the electrode substrate and the electrode on the side of the insertion part 102, which are not shown in the drawings, press the electric conductive rubber 139B which is an elastic body, thereby compressing the electric conductive rubber 139B. For this reason, because the electrode on the side of the insertion part 102 and the electrode pattern 138c of the first substrate 138A come into contact closely with both sides of the electric conductive rubber 139B, respectively, so as to sandwich the conductive electric conduction rubber 139B, it becomes possible to energize reliably from the main body 103 to the LED substrate 133A which is an electric instrument prepared in Adapter 130A together with thinning diameters of the adapter 130A and of the insertion part 102.

It should be noted that although an electrode substrate which corresponds to the second substrate is disposed to the insertion part side in the example shown in the drawings, of course various modifications similar to the fifth embodiment can be performed; for example, it is possible to dispose the electrode substrate which corresponds to the second substrate to the adapter 130A side, similar to the fifth embodiment.

Moreover, although the shape of the electrode of the fifth embodiment is different from that of the electrode of the sixth embodiment, it is possible to form the electrode of the adapter 130 for direct vision in the fifth embodiment into the same shape as the electrode of the adapter for side viewing. In such a case, it becomes possible to exchange the adapter for direct vision, with the adapter for side viewing.

Seventh Embodiment

Next, the seventh embodiment of the endoscope apparatus of the present invention will be explained based on FIGS. 27 and 28. It should be noted that the same reference numerals are given to the corresponding portions as in the above embodiments, and the detailed explanation thereof is omitted.

Now, although the fifth and the sixth embodiments mentioned above explained the endoscope apparatus of which the adapters 130 and 130A were constituted to be detachably attached to the tip end part of the insertion part 102, in the embodiment which will be explained below, a case in which the tip end member which is equipped with electric instruments is constituted to be detachably attached to the tip end part of the adapter is explained.

Figure 27:
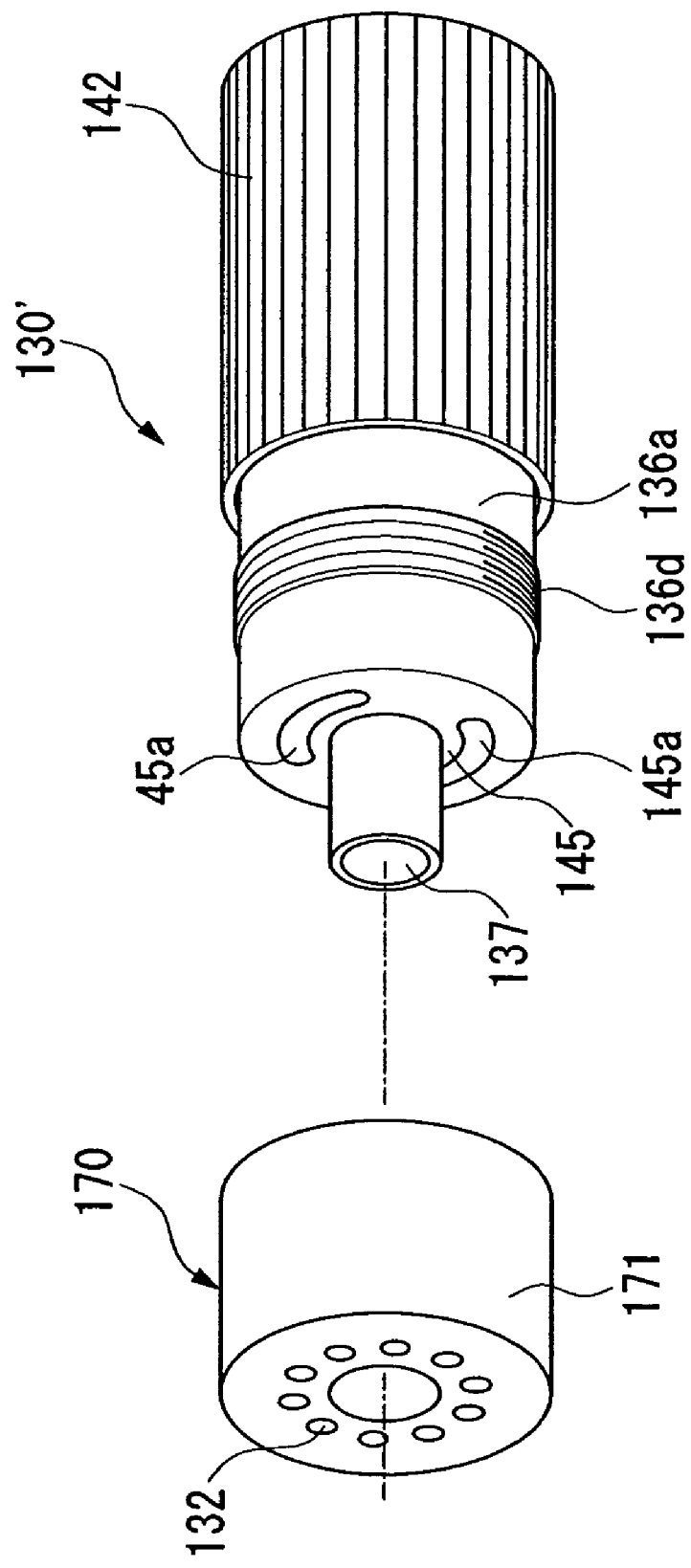
FIG. 27 is an exploded diagram view showing the adapter for direct vision constituted so that the tip end member is detachably attached, as the third embodiment of the present invention.
Figure 28:
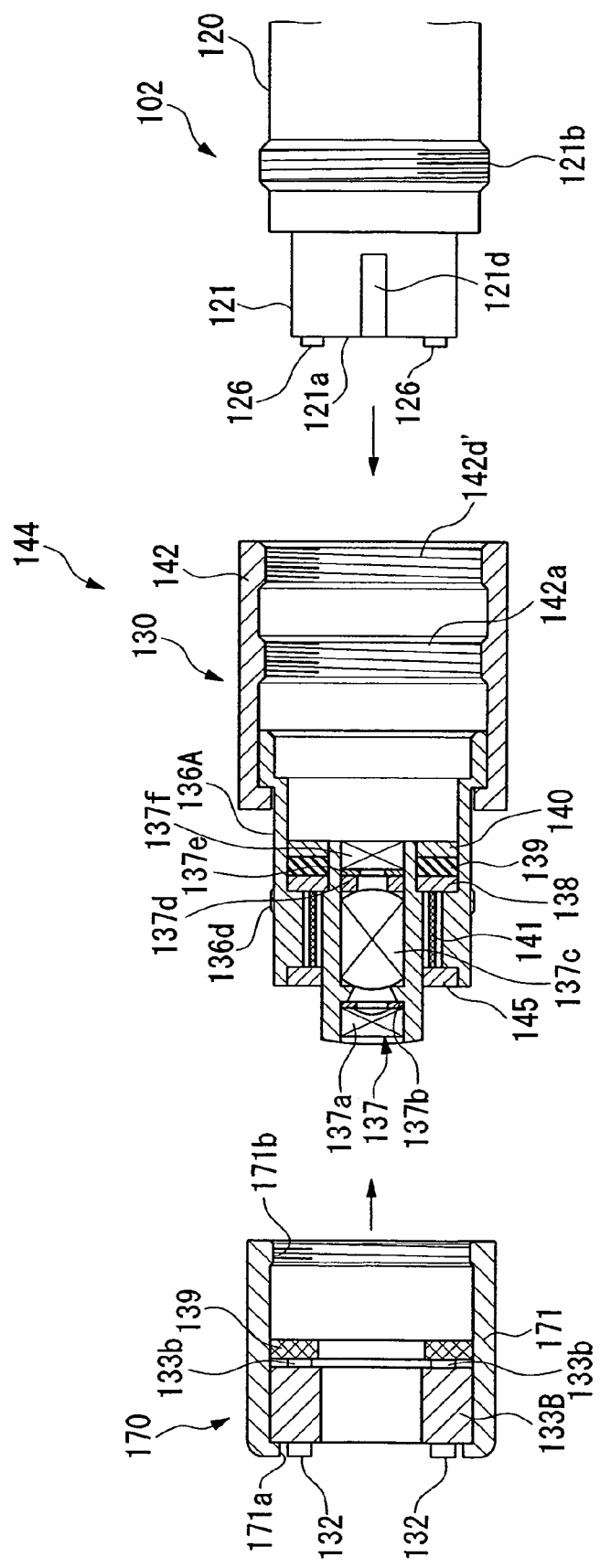
FIG. 28 is a principal part sectional view of FIG. 27.

In the adapter 130' for direct vision shown in FIGS. 27 and 28, the illuminating unit (tip end member) 170 which is equipped with LED illuminating devices 132 which are electric instruments is constituted as an independent body and one being detachably attached. The illuminating unit 170 is a part which is shareable with a many kinds of adapter 130' each of which specification is different from each other, and the illuminating unit 170 is detached and attached to the tip end part of each adapter, while being exchanged. That is, the adapter 130' is one body in which the main body 144 of an adapter and the illuminating unit 170 are united.

The illuminating unit 170 is constituted from a cylindrical outer frame member 171, the LED substrate 133B formed into a toroidal shape, and an electric conductive rubber 139, and both the LED substrate 133B and the electric conductive rubber 139 are inserted in the outer frame member 171. The outer frame member 171 is equipped with an engagement part 171a which is formed by bending the tip end of the outer frame member 171 inwardly, to which the front face perimeter end of the LED substrate 133B is abutted, thereby positioning the LED substrate 133B. A pair of electrodes (the third electrode) 133b project from the back face of the LED substrate 133B, respectively, and the electric conductive rubber 139 is disposed so as to be in contact with the electrodes 133b.

The illuminating unit 170 mentioned above is connected and united with the main body 144 of an adapter by screwing the inner thread part 171b formed inside the back end part of the outer frame member 171 with the outer thread part 136b which is formed on the perimeter side of the LED presser 136a.

The main body 144 of an adapter is substantially the same constitution as that shown in FIG. 14A, except for the portion relating to the illuminating unit 170 and the third substrate 145 which was mentioned above. The front surface of the third substrate 145 which is equipped with a pair of electrode patterns (the fourth electrode) 145a is exposed, and the back surface thereof is electrically connected to the electric wire 141.

In the adapter 130' having such a constitution, by disposing the illuminating unit 170 to the predetermined position of the main body 144 of an adapter, the electric conductive rubber 139 is interposed between the LED substrate 133B and the third substrate 145 and is compressed. For this reason, while the electric conductivity of the compressed electric conductive rubber 139 is improved, the electrode pattern 145a of the third substrate 145 and the electrode 133b of the LED substrate 133B come into contact closely with the electric conductive rubber 139, respectively, thereby enabling reliable and superior energizing. It should be noted that, as the fifth embodiment mentioned above, it is possible to attain reliable and superior energizing at the gap between the main body 144 of an adapter and the insertion part 102 by interposing the electric conductive rubber 139 between the main body 144 of an adapter and the insertion part 102.

Figure 29A:
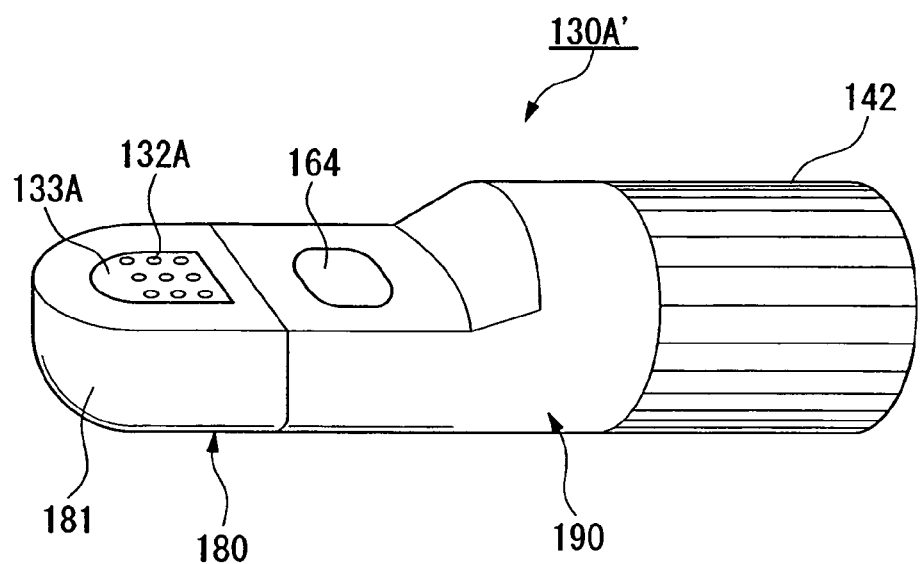
FIGS. 29A and 29B show the first modification of the third embodiment of the present invention.
Figure 29B:
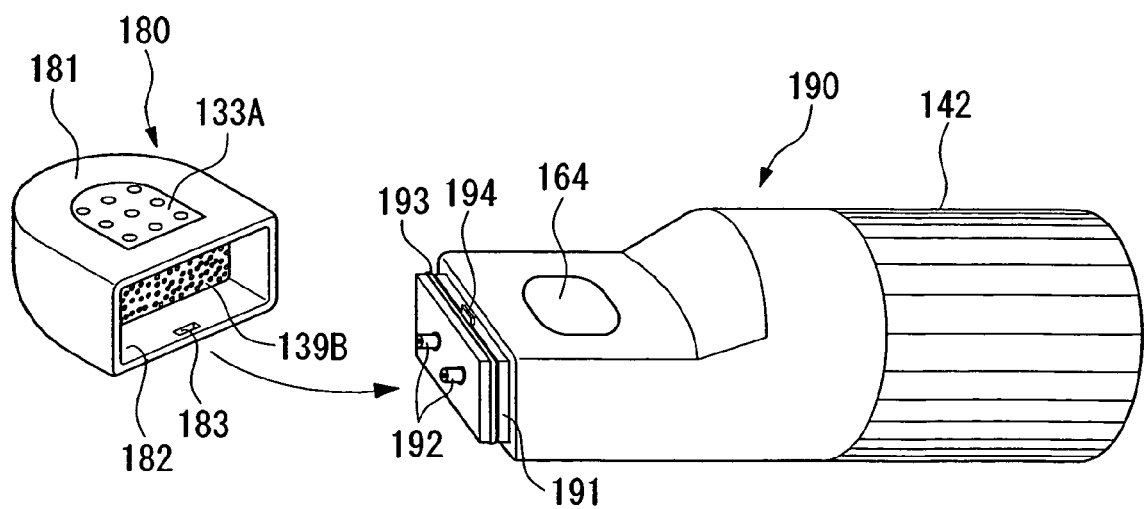
Figure 30:
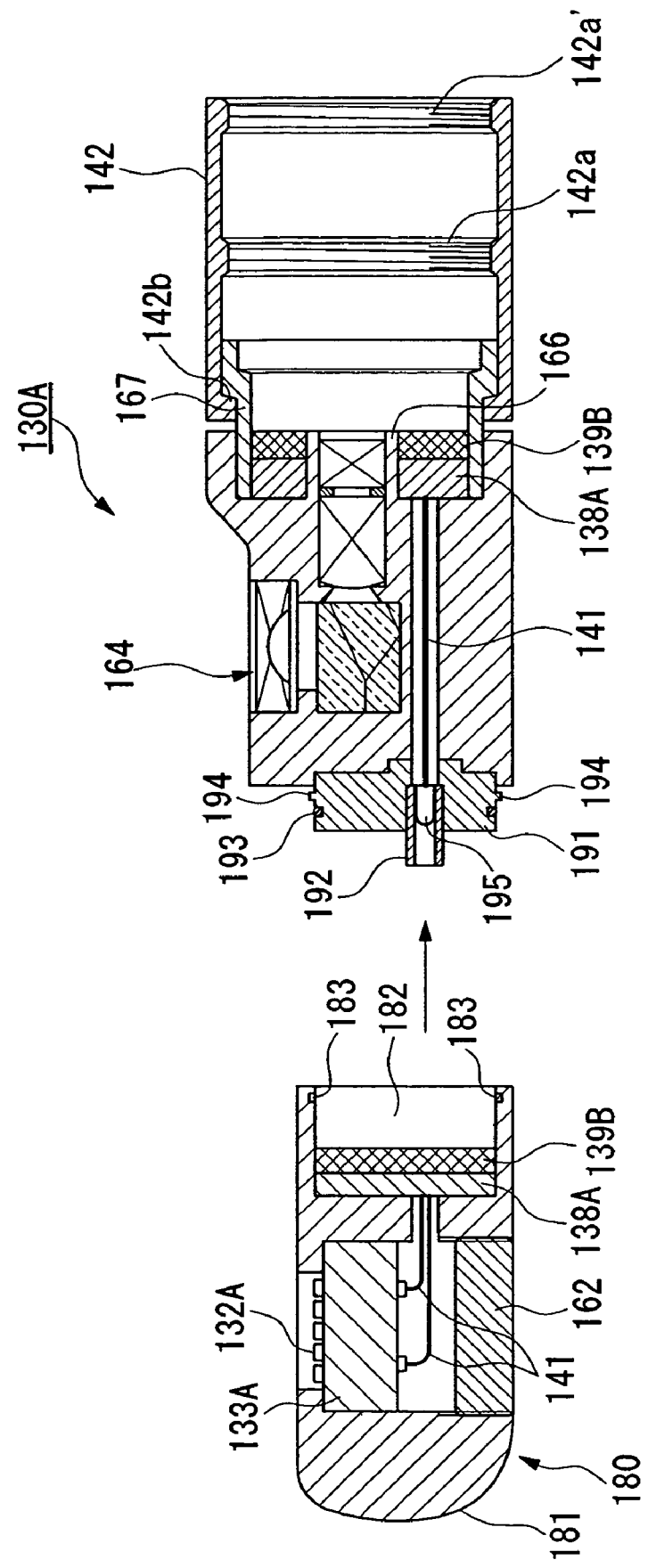
FIG. 30 is a sectional view of FIG. 29B.

Next, the example in which the present invention is applied to the adapter 130A' for side viewing will be explained as the first modification of the seventh embodiment based on FIGS. 29A, 29B, and 30. It should be noted that the same reference numerals are given to the corresponding portions as in the above embodiments, and the detailed explanation thereof is omitted.

The illuminating unit 180 in this case becomes a unified adapter 130A', by joining the back end part of the outer frame member 181 with the tip end part of the main body 190 of an adapter. In the example shown in the drawing, the connection concave portion 182 of approximately rectangular shape is formed on the back end part of the outer frame member 181, and one pair of engagement concave parts 183 for holding a connection state is formed in the inner circumference surface of the connection concave portion 182 up and down.

Moreover, in the connection concave portion 182, the electric conductive rubber 139 is disposed such that one surface of thereof faces the opening side. The electric conductive rubber 139B is arranged in parallel to the first substrate 138A which is electrically connected to the LED substrate 133A through the electric wire 141, so as to be in contact with the first substrate 138A. It should be noted that the LED substrate 133A and the sealing member 162 are substantially identical with the constitution of the tip end of the second embodiment mentioned above.

The tip end part at the main body 190 of an adapter side is formed to be a connection convex part 191 of the projection shape which can be joined to the connection concave portion 182, and a pair of electrodes 192 project from the tip end surface thereof. And while the O-ring 193 is attached in all circumferences, the engagement projection part 194 of one pair of upper and lower sides are formed in the perimeter side of connection convex part 191. It should be noted that the gap between the electrode 192 and the first substrate 138A at the main body 190 of an adapter side is electrically connected through the electric wire 141 of which one side is equipped with the terminal electrode 195.

In the adapter 130' having such a constitution, by disposing the illuminating unit 180 to the predetermined position of the main body 190 of an adapter, the electric conductive rubber 139B is interposed between the first substrate 138A at the illuminating unit 180 side and the electrode 192 and is compressed. For this reason, while the electric conductivity of the compressed electric conductive rubber 139B is improved, the electrode pattern of the first substrate 138A and the electrode 192 of the connection convex part 191 come into contact closely with the electric conductive rubber 139B, respectively, thereby enabling reliable and superior energizing. It should be noted that, as the sixth embodiment mentioned above, it is possible to attain reliable and superior energizing at the gap between the main body 190 of an adapter and the insertion part 102 by interposing the electric conductive rubber 139B between the main body 190 of an adapter and the insertion part 102.

It should be noted that the present invention is not limited to any of the above embodiments. That is, the present invention can be suitably modified as long as it does not deviate from the spirit of the present invention, for example, the present invention is applicable to electric instruments other than the LED illuminating such as a various sensors.

In the above endoscope apparatus of the present invention, an anisotropic electric conductive elastic member is disposed between the first electrode and the second electrode, such that the anisotropic electric conductive elastic member is interposed between the first electrode and the second electrode so as to be compressed therebetween, the gap between the first electrode and the second electrode is electrically connected, thereby an energizing state reliably. For this reason, because when the tip end member is attached to the tip end part of the insertion part, each of the first electrode and the second electrode comes into contact closely with the anisotropic electric conductive elastic member from both sides so as to compress it, only a thickness direction thereof becomes an energizing state, due to characteristics of the anisotropic electric conductive elastic member. Therefore, it becomes an electrode constitution having a superior electric conductivity. Moreover, the constitution of interposing the anisotropic electric conductive elastic member in the state of piling in an axial direction is advantageous for reducing the diameter of the insertion part.

Moreover, by constituting the tip end part (illuminating unit) which is equipped with the electric instruments of the tip end member (adapter) as a detachably attached independent body, it becomes possible to make the tip end part be commonly used, and hence it becomes possible to reduce the cost and storing space for the tip end member of which there are various kinds.

In this case, by disposing the anisotropic electric conductive elastic member between the third electrode at the tip end part side and the fourth electrode at the tip end member side, the anisotropic electric conductive elastic member is interposed between the third electrode and the fourth electrode so as to be compressed therebetween, thereby forming an electrical connection between the third electrode and the fourth electrode to obtain a reliable energizing state therebetween.

As mentioned above, although the desirable case of the operation of the present invention was explained, the present invention is not limited to these cases of the operation. It is the range which does not deviate from the meaning of the present invention, and addition of composition, an abbreviation, substitution, and other change are possible. The present invention is not limited by the explanation mentioned above and is limited by only the range of an attached claim.

What is claimed is:

1. An endoscope apparatus comprising:
a connector having a light emitting diode;
an apparatus body side connector to which the connector is detachably connectable;
a main electrical power supply which provides current to the light emitting diode from the apparatus body side connector; and
an energizing controlling device which controls the main electrical power supply to start providing current to the light emitting diode only after a first predetermined period of time after the connector and the apparatus body side connector are initially substantially connected,
wherein the energizing controlling device comprises:
first and second electrodes which are provided on the apparatus body side connector and each of which are electrically engaged and disengaged with the light emitting diode with a time differential at the times of the connection and disconnection; and a switching circuit which is connected to one of the first electrode and the second electrode, which is engaged later; and disengaged earlier, than the other.

2. An endoscope apparatus comprising:

a connector having a light emitting diode;

an apparatus body side connector to which the connector is detachably connectable;

a main electrical power supply which provides current to the light emitting diode from the apparatus body side connector; and an energizing controlling device which controls the main electrical power supply to start providing current to the light emitting diode only after a first predetermined period of time after the connector and the apparatus body side connector are initially substantially connected, wherein a first electrode is provided on the connector having the light emitting diode;

a second electrode is provided on the apparatus body side connector; and an elastic member made of an anisotropic conductor is provided between the first electrode and the second electrode.

3. The endoscope apparatus as recited in claim 2, wherein the elastic member includes an insulating member and electrical conductive members dotted thereon as extending through the insulating member in a direction between the first and second electrodes.

4. The endoscope apparatus as recited in claim 2, wherein the elastic member has a sheet shape.

5. The endoscope apparatus as recited in claim 2, wherein the elastic member is in contact with the first electrode.

6. The endoscope apparatus as recited in claim 2, wherein the elastic member is in contact with the second electrode.

7. The endoscope apparatus as recited in claim 2, wherein the first electrode is constituted from an electrode pattern formed on a resin board.

8. The endoscope apparatus as recited in claim 7, wherein the electrode pattern is an arc shape.

9. The endoscope apparatus as recited in claim 2, wherein the second electrode is comprised of a columnar member with an outer surface covered by insulating material.

10. The endoscope apparatus as recited in claim 2, wherein the elastic member has a toroidal shape.

* * * * *